(12) United States Patent
Stetz et al.

(10) Patent No.: US 8,204,575 B2
(45) Date of Patent: Jun. 19, 2012

(54) LOCATING GUIDE

(75) Inventors: Eric M. Stetz, Lino Lakes, MN (US);
Eric H. Bonde, Minnetonka, MN (US);
Yelena G. Tropsha, Plymouth, MN
(US); Thomas Chun, Marietta, GA (US)

(73) Assignee: Medtronic, Inc., Minneapolis, MN (US)

( * ) Notice: Subject to any disclaimer, the term of this patent is extended or adjusted under 35 U.S.C. 154(b) by 1111 days.

(21) Appl. No.: 11/835,296

(22) Filed: Aug. 7, 2007

(65) Prior Publication Data

US 2008/0039866 A1  Feb. 14, 2008

Related U.S. Application Data

(60) Provisional application No. 60/932,961, filed on Aug. 11, 2006.

(51) Int. Cl.
*A61B 5/05* (2006.01)
(52) U.S. Cl. .................................. 600/424; 600/426
(58) Field of Classification Search .................. 600/424, 600/426, 431
See application file for complete search history.

(56) References Cited

U.S. PATENT DOCUMENTS

| | | | |
|---|---|---|---|
| 2,245,350 A | | 6/1941 | Marshall |
| 3,001,070 A | * | 9/1961 | Davis, Jr. et al. ............... 378/52 |
| 4,541,432 A | | 9/1985 | Molina-Negro et al. |
| 4,915,112 A | * | 4/1990 | Singer ............................ 600/426 |
| 5,216,700 A | * | 6/1993 | Cherian ......................... 378/163 |
| 5,242,455 A | * | 9/1993 | Skeens et al. .................. 606/130 |
| 5,284,153 A | | 2/1994 | Raymond et al. |
| 5,311,878 A | | 5/1994 | Brown et al. |
| 5,531,737 A | | 7/1996 | Schade |
| 5,560,372 A | | 10/1996 | Cory |
| 5,775,331 A | | 7/1998 | Raymond et al. |
| 5,810,742 A | | 9/1998 | Pearlman |
| 6,055,452 A | | 4/2000 | Pearlman |
| 6,360,750 B1 | | 3/2002 | Gerber et al. |

(Continued)

FOREIGN PATENT DOCUMENTS

EP  1 239 768 B1  9/2002

(Continued)

OTHER PUBLICATIONS

Notification of Transmittal of the International Preliminary Report on Patentability dated Nov. 6, 2009 for corresponding PCT Application No. PCT/US2008/070726 (13 pgs.).

(Continued)

*Primary Examiner* — Tse Chen
*Assistant Examiner* — Peter Luong
(74) *Attorney, Agent, or Firm* — Shumaker & Sieffert, P.A.

(57) ABSTRACT

A locating guide for locating a target tissue site within a patient includes a body, a first substantially radiopaque reference marker on the body, and a second substantially radiopaque reference marker extending from a major surface of the body. The reference markers provide reference points that extend in at least two dimensions, and may be useful for registering a medical image of tissue with an actual location on or within the patient in order to more accurately and precisely locate a target tissue site within the patient. In some embodiments, the second reference marker is oriented at a predetermined angle relative to the major surface of the body, and provides a guide that a clinician may reference in order to orient a medical element introducer when introducing the introducer into the patient to access a particular target tissue site.

36 Claims, 14 Drawing Sheets

U.S. PATENT DOCUMENTS

| | | |
|---|---|---|
| 6,405,732 B1 | 6/2002 | Edwards et al. |
| 6,512,958 B1 | 1/2003 | Swoyer et al. |
| 6,564,079 B1 | 5/2003 | Cory et al. |
| 6,760,616 B2 | 7/2004 | Hoey et al. |
| 6,847,849 B2 | 1/2005 | Mamo et al. |
| 6,974,456 B2 | 12/2005 | Edwards et al. |
| 7,050,848 B2 | 5/2006 | Hoey et al. |
| 7,204,826 B2 | 4/2007 | Tremaglio et al. |
| 2002/0072686 A1 | 6/2002 | Hoey et al. |
| 2002/0147485 A1 | 10/2002 | Mamo et al. |
| 2003/0216662 A1 | 11/2003 | Jersey-Willuhn et al. |
| 2004/0015176 A1 | 1/2004 | Cosman |
| 2004/0102721 A1 | 5/2004 | McKinley |
| 2004/0103903 A1 | 6/2004 | Falahee |
| 2004/0181165 A1 | 9/2004 | Hoey et al. |
| 2005/0045191 A1 | 3/2005 | McKinley |
| 2005/0109855 A1 | 5/2005 | McCombs |
| 2005/0240238 A1 | 10/2005 | Mamo et al. |
| 2006/0004422 A1 | 1/2006 | DeRidder |
| 2006/0085048 A1 | 4/2006 | Cory et al. |
| 2006/0085049 A1 | 4/2006 | Cory et al. |

FOREIGN PATENT DOCUMENTS

| | | |
|---|---|---|
| WO | WO 01/43630 | 6/2001 |
| WO | WO 01/87154 | 11/2001 |
| WO | WO 02/09584 | 2/2002 |
| WO | WO 2004/047874 | 6/2004 |
| WO | WO 2005/087314 | 9/2005 |

OTHER PUBLICATIONS

"Notification of Transmittal of the International Search Report and the Written Opinion of the International Searching Authority, or the Declaration," dated Nov. 13, 2008 for corresponding PCT Application No. PCT/US2008/070726 (19 pgs.).

Reply to Written Opinion dated Feb. 13, 2009 for corresponding PCT Application No. PCT/US2008/070726 (15 pgs.).

U.S. Appl. No. 11/835,290 to Dinsmoor et al., entitled "Guided Medical Element Implantation," filed Aug. 7, 2007.

\* cited by examiner

LOCATING GUIDE

This application claims the benefit of U.S. Provisional Application No. 60/932,961, entitled "GUIDED MEDICAL LEAD IMPLANTATION," and filed on Aug. 11, 2006, the entire content of which is incorporated herein by reference.

TECHNICAL FIELD

The invention relates to medical devices and, more particularly, the implantation of medical devices.

BACKGROUND

Medical systems for tissue therapy often require the implantation of one or more medical elements proximate to a target tissue site. The medical element may be, for example, a medical lead to deliver electrical stimulation energy to the tissue or a catheter to deliver a fluid to the tissue. In order to implant the medical element in a patient, a clinician may generate a medical image of the target tissue site for the medical element and guide the medical element into the patient based on the generated image.

For some tissue stimulation applications, an electrical stimulation lead is implanted near a sacral nerve, which is a nerve bundle within the sacrum, a large triangular bone situated at the lower part of the vertebral column and at the upper and back part of the human pelvic cavity. There are multiple sacral nerves that pass through anterior and posterior sacral foramina of the sacrum. The lead may include one or more stimulation electrodes, one or more sensing electrodes, or combinations thereof.

Electrical stimulation of one or more sacral nerves may eliminate or reduce some pelvic floor disorders by influencing the behavior of the relevant structures, such as the bladder, sphincter and pelvic floor muscles. Pelvic floor disorders include urinary incontinence, urinary urge/frequency, urinary retention, pelvic pain, bowel dysfunction, and male and female sexual dysfunction. The organs involved in bladder, bowel, and sexual function receive much of their control via the second, third, and fourth sacral nerves, commonly referred to as S2, S3 and S4 respectively. Electrical stimulation is typically delivered to at least one of the S2, S3, or S4 sacral nerves using an electrical stimulator, which is coupled to a stimulation lead that is implanted on a temporary or permanent basis proximate to the relevant sacral nerve.

In some cases, a medical element of a medical system is implanted through a sacral foramen (a single foramina) of a patient. For example, if selective stimulation of the S3 sacral nerve is desired, a medical lead may be introduced into the sacral foramen corresponding to the S3 sacral segment, which is commonly referred to as the "S3 sacral foramen." In one technique, a hollow introducer needle is advanced through the S3 foramen and the lead is advanced through a lumen of the hollow introducer needle until one or more electrodes near a distal end of the lead are positioned near the S3 sacral nerve. Stimulation energy is applied through the lead to the electrode to test the S3 nerve response. If necessary, the one or more electrodes are moved back and forth to locate the most efficacious location.

Once in position, the lead may be secured by suturing the lead body to subcutaneous tissue posterior to the sacrum or using an anchoring mechanism such as tines carried by the lead, sutures or another technique. The lead may then be attached directly or indirectly (e.g., via an extension) to the output of an implantable electrical stimulator, although in some cases, the lead may be attached to an external pulse generator for temporary trial stimulation.

SUMMARY

In general, the invention is directed to a locating guide for locating a target tissue site. In some embodiments, the target tissue site includes a target nerve site, which may be, for example, a location of a target nerve or a location of an anatomical structure providing access to the nerve. The locating guides described herein include reference markers that are visible in a medical image, such as a radiographic image. In particular, a locating guide includes at least a first reference marker and a second, lateral reference marker protruding from a body of the locating guide in a different direction than the first reference marker, if the first reference marker protrudes from the body at all. The first and second reference markers provide reference points for registering a medical image of the patient, where the medical image may include an image of the target tissue site at an actual location on the patient. Together, the first and second reference markers provide visual reference points that extend in at least two dimensions, thereby increasing the possibility that a reference marker will be visible in a medical image. That is, the locating guide includes reference markers that are visible from at least two different perspectives.

The locating guide may be placed on a skin surface of a patient proximate to the target tissue site. In some embodiments, at least one reference marker of the locating guide may be used to align the locating guide with a boney landmark of a patient. A medical image of the locating guide and underlying tissue (proximate to the locating guide) may be generated to identify an approximate location of a target tissue site relative to the locating guide. Based on the medical image, the clinician may associate one or more reference markers of the locating guide with the location of the target tissue site. The clinician may then register the relevant portions of the medical image, such as the reference markers associated with the target tissue site and/or the target tissue site image, to an actual location on or within the patient. For example, the clinician may register the image of the reference markers associated with the target tissue site to the actual reference markers, and determine an approximate location of the target tissue site based on the actual location of the reference markers.

If desired, the clinician may introduce a medical element into the patient using the one or more reference markers associated with the target tissue site as a guide for locating the target tissue site. The medical element may be, for example, a medical lead, electrical stimulator or catheter. In some embodiments, a body of the locating guide defines an aperture that provides an opening in the locating guide through which the clinician may access the target tissue site. In some cases, the clinician may implant the medical element with the aid of an introducer needle, which may be percutaneously introduced into the patient or through an incision. In some embodiments, the second reference marker extends from the body of the locating guide at an angle and indicates the angle at which the clinician may orient the introducer needle relative to the skin surface of the patient in order to access a particular target tissue site, such as a sacral foramen. In this way, the second reference marker may also be a guide for orienting an introducer needle in order to more accurately access a target tissue site.

In one embodiment, the invention is directed to a target tissue site locating guide comprising a body defining a major surface, a first substantially radiopaque reference marker on the body, and a second substantially radiopaque reference marker extending from the major surface of the body.

In another embodiment, the invention is directed to a locating guide comprising a body configured to overlay a skin surface of a patient proximate to a sacrum of the patient, and a radiopaque reference marker on the body and configured to extend away from the skin surface of the patient at an angle when the body is positioned on the skin surface. The angle indicates an orientation for introducing an introducer into the patient to access a sacral foramen of the sacrum.

In another embodiment, the invention is directed to a method comprising positioning a locating guide on a skin surface of a patient. The locating guide comprises a body, a first radiopaque reference marker on the body, and a second radiopaque reference marker on the body and configured to extend away from the skin surface of the patient when the locating guide is positioned on the skin surface. The method further comprises generating an image of at least a portion of the locating guide and at least a portion of tissue of the patient proximate to the locating guide with a medical imaging device, and registering the image with an actual location on or within the patient based on at least one of the first or second reference markers.

The details of one or more embodiments of the invention are set forth in the accompanying drawings and the description below. Other features, objects, and advantages of the invention will be apparent from the description and drawings, and from the claims.

DETAILED DESCRIPTION

The invention relates to a locating guide for locating a target tissue site within a patient. The target tissue site may be a target nerve site, which may refer to the location of a target nerve or a location of an anatomical structure providing access to the nerve. As one example, the target nerve site may be a sacral nerve or a sacral foramen, through which a sacral nerve is accessible. The locating guides described herein include reference markers that, together with a medical imaging device, such as fluoroscopy device, provide a clinician with information concerning the location of a target tissue site within the patient. In some embodiments, determining the location of a target tissue site may be useful for implanting a medical element, such as, but not limited to, a medical lead, electrical stimulator or catheter, proximate to the target tissue site.

Various embodiments of the invention may be applicable to different therapeutic applications requiring implantation of a medical element, such as neuromodulation by electrical stimulation of or drug delivery to one or more sacral nerves, pudendal nerves (including perineal and/or dorsal nerve branch), genitofemoral nerves (including genital and/or femoral nerve branch), ilioinguinal nerves, and iliohypogastric nerves. Such neuromodulation techniques may be provided to alleviate a variety of symptoms or disorders, including pelvic pain, urinary incontinence, fecal incontinence, and sexual dysfunction. The locating guides described herein may be applicable to a variety of other therapeutic applications and tissue sites, including a variety of peripheral nerve sites. For purposes of illustration, however, the disclosure will refer to electrical stimulation of one or more sacral nerves, and will refer to a "target nerve site," although the locating guides described herein may also be useful for locating other target tissue sites.

Figure 1:
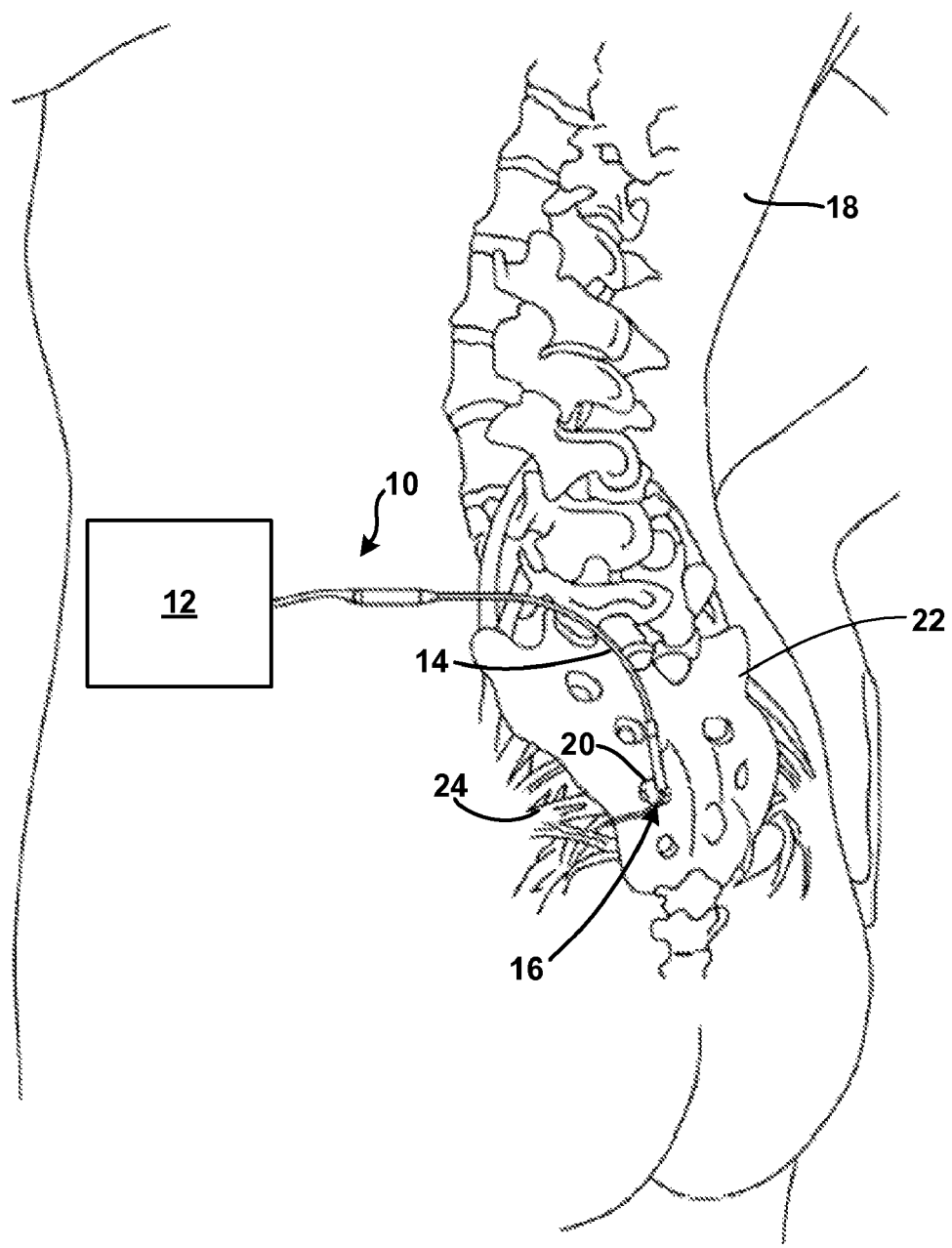
FIG. 1 is a schematic perspective view of a therapy system, which includes a medical device coupled to medical element that has been implanted proximate to a target tissue site located with a locating guide.

FIG. 1 is a schematic perspective view of therapy system 10, which includes medical device 12 coupled to implanted medical element 14. Implanted medical element 14 has been implanted proximate to target nerve site 16, which has been located with the aid of a locating guide (described in further detail below). In the embodiment of therapy system 10 shown in FIG. 1, target nerve site 16 is sacral foramen 20 of sacrum 22. Sacral foramen 20 provides access to sacral nerve 24. However, in alternate embodiments, target nerve site 16 may be any suitable nerve site in patient 18, whether it is a nerve or an anatomical structure providing access to the nerve, and may be selected based on, for example, a therapy program selected for a particular patient 18. Medical device 12 may be subcutaneously implanted in the body of a patient 18 (e.g., in a chest cavity, lower back, lower abdomen, or buttocks). The type of medical device 12 and implanted medical element 14 incorporated into therapy system 10 may also depend upon the therapeutic application.

For example, in the embodiment shown in FIG. 1, medical device 12 is an electrical stimulator (either implantable or external), which is directly or indirectly (e.g., via an extension) coupled to medical element 14, which is a stimulation lead. Medical device 12 provides a programmable stimulation signal (e.g., in the form of electrical pulses or a continuous signal) that is delivered to target nerve site 16 by stimulation lead 14, and more particularly, via one or more stimulation electrodes carried by lead 14. In some cases, an electrical stimulator may also be referred to as a signal generator or a neurostimulator. In another embodiment, lead 14 may include one or more sense electrodes to permit medical device 12 to sense electrical signals from target nerve site 19, such as to sense one or more physiological parameters of patient 18 (e.g., blood pressure, temperature or electrical activity). Furthermore, in some embodiments, medical 12 may be coupled to two or more leads, e.g., for bilateral or multi-lateral stimulation and/or sensing.

While medical element 14 is primarily referred to as a "medical lead" for the remainder of the description, in other embodiments, medical element 14 may be any suitable medical element. For example, in another embodiments, medical device 12 may be a fluid delivery device, such as a drug pump, and medical element 14 may be a catheter that is placed to deliver a fluid (e.g., pharmaceutical agents, insulin, pain relieving agents, gene therapy agents or the like), from medical device 12 to target nerve site 16. In yet other embodiments, medical element 14 may be a substantially self-contained device that is not coupled to medical device 12, and therapy system 10 may not include medical device 12. For example, in some embodiments, medical element 14 may be a leadless microstimulator, which includes a substantially self-contained device that includes stimulation and/or sensing electrodes and the associated electronics (e.g., controls, power source, and etc.) or a microstimulator with a lead that includes at least one stimulation and/or sensing electrode.

In some cases, a clinician may generate a real-time or still image of the relevant tissue of patient 18 using a medical imaging device, such as an x-ray machine or a fluoroscope, in order to locate target nerve site 16. For example, a fluoroscopic image may be used to generate a real-time image of at least a portion of sacrum 22 of patient 18 in order to locate the target sacral foramen 20. The clinician may locate target nerve site 16 and guide medical lead 14 proximate to sacral nerve 24 with the aid of the fluoroscopic image. Due at least in part to the curvature of sacrum 22 and/or the positioning of patient 18, and in particular, the positioning of sacrum 22 relative to the fluoroscopic imager, the image of sacrum 22 may not clearly illustrate the target sacral foramen 20. In some cases, the fluoroscopic image of sacrum 22 may not illustrate the target sacral foramen 20 or insufficiently illustrate target sacral foramen 20 (e.g., illustrate foramen 20 from a poor angle), such that the fluoroscopic image provides the clinician with insufficient guidance as to the location of target nerve site 16.

Even if the target sacral foramen 20 is visible in the fluoroscopic image, the image of sacral foramen 20 may not be representative of the size or shape of the sacral foramen 20 or the relative location of the target sacral foramen 20 relative to a boney landmark or another internal reference point. In particular, the fluoroscopic image angle and/or the curvature of sacrum 22 may impart a skew to the size and shape of the imaged foramen 20. Again, this may provide the clinician with little guidance as to the location of target nerve site 16, and, in some cases, the clinician may inaccurately read the medical image and incorrectly determine a location of the target sacral foramen 20. The inaccuracies in reading the medical image may arise from, for example, how the clinician relates the medical image to an actual location on the patient. The fluoroscopic image angle and/or the curvature of sacrum 22 may misguide the clinician in identifying the location of sacral foramen 20 relative to other portions of sacrum 22 or patient 18.

A locating guide described herein provides one or more useful, visible reference markers that the clinician may use to more accurately register a medical image (e.g., a fluoroscopic image) to an actual location on or within the patient. The locating guide may help minimize any degradation in the usefulness of the medical image because of possible misalignment between the imaging device (e.g., a fluoroscope) and target nerve site 16 and/or a possible misregistration between the image and the patient by the clinician. Target nerve site 16 may be sacral foramen 20 or another site within patient 18. A clinician may place the locating guide on a skin surface of patient 18 proximate to target nerve site 16 and a medical image may be taken of the locating guide and portions of tissue underlying the skin proximate to the locating guide. The clinician may associate one or more features of the locating guide, such as distance reference markers, lateral markers that protrude from the locating guide body, or centerline reference markers, shown in the medical image with the image of target nerve site 16. For example, the clinician may identify one or more of the reference markers as being closest to the target nerve site. The clinician may then approximate the location of target nerve site 16 based on the relevant reference markers of the locating guide. In this way, the one or more features of the locating guide provide externally visible reference points that a clinician may use to register a medical image, and in particular, a target nerve site shown in the medical image, to an actual location on or within patient 18.

Figure 2A:
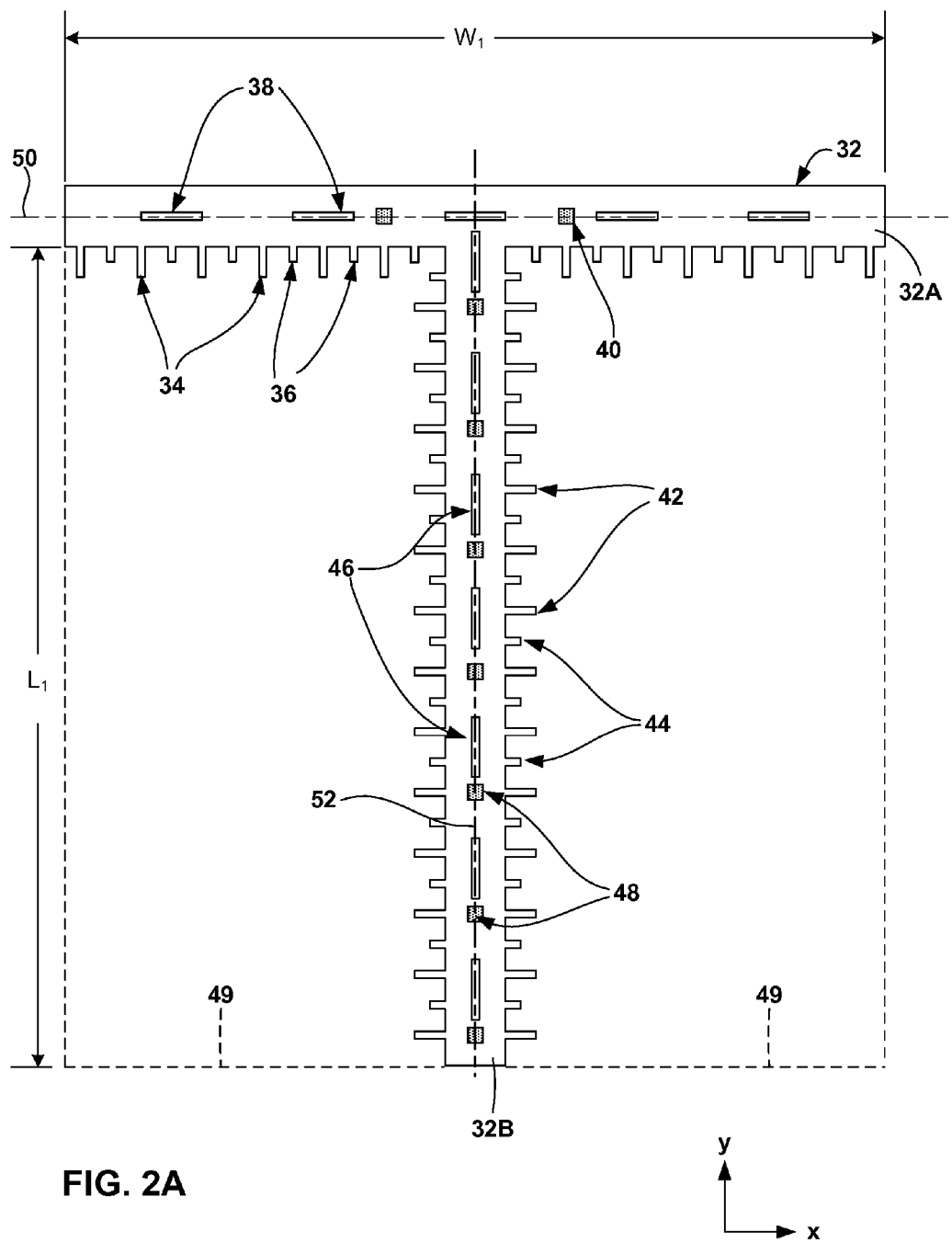
FIGS. 2A and 2B illustrate a plan and a side view, respectively, of a locating guide in accordance with an embodiment of the invention.
Figure 2B:
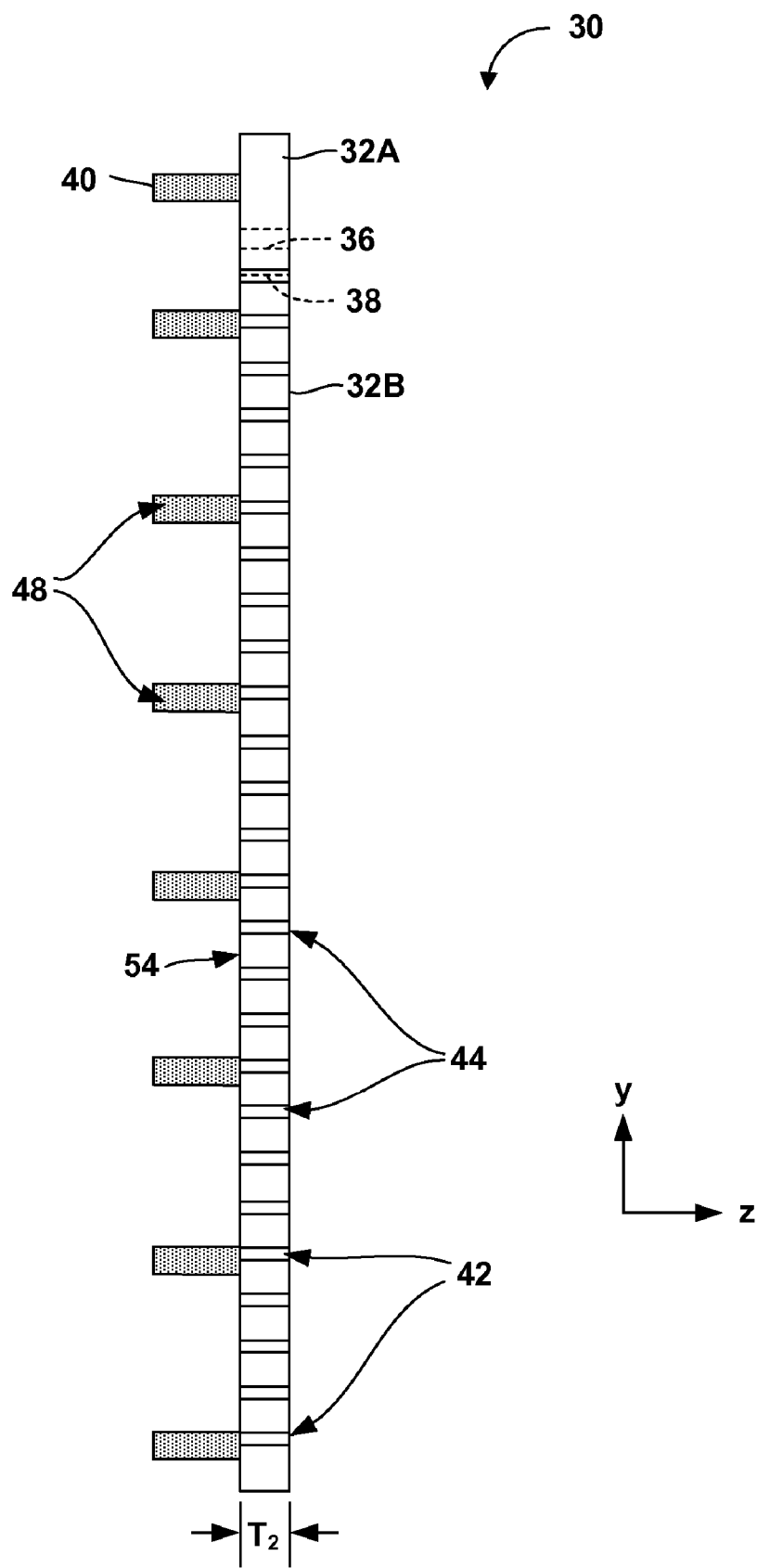

FIGS. 2A and 2B illustrate a top view and a side view, respectively, of locating guide 30 in accordance with an embodiment of the invention. Reference to a "top view" and "side view" herein refers generally to the orientation of the views relative to each other, and is not intended to indicate that the views necessarily illustrate a top and side of the shown locating guide. The "top" and "side" views are merely orthographic projection views.

Locating guide 30 may be used to guide a clinician during a target nerve site 16 location technique. In general, locating guide 30 is placed on a patient's skin surface and provides an externally visible reference point that is also visible in a medical image (e.g., a fluoroscopic image). For example, a clinician may position locating guide 30 on a skin surface of patient 18 proximate to sacrum 22 in order to aid in locating a target sacral foramen 20 (FIG. 1). Locating guide 30 includes body 32, which defines first portion 32A and second portion 32B. Locating guide 30 further includes distance reference markers 34, 36, centerline reference markers 38, and lateral reference markers 40 along first portion 32A of body 32, and distance reference markers 42, 44, centerline reference markers 46, and lateral reference markers 48 along second portion 32B. Reference markers 34, 36, 38, 40, 42, 44, 46, and 48 may each be integrally formed with body 32 (e.g., molded, casted, extruded, stamped or punched from body 32, printed onto body 32, etc.) or fixed to body 32 (e.g., via an adhesive, ultrasonic welding, or otherwise).

Locating guide 30 is preferably formed of a material including a color that allows locating guide 30 to be easily visually distinguished from skin on which it is placed. In addition, one or both sides of locating guide 30 may define a "skin contact side," which is a surface of locating guide 30 that is intended to contact a patient's skin. The skin contact side of locating guide 30 may be chemically and biologically inert to limit any reaction with skin or other surfaces and materials (e.g., common sterilizing agents such as isopropyl alcohol or iodine) that may be contacted by locating guide 30. In some embodiments, locating guide 30 may be disposable after use with a single patient. In other embodiments, locating guide 30 may be reusable. Of course, if locating guide 30 is reused for multiple patients, it may be desirable to sterilize locating guide 30.

Body 32 may be constructed of any suitable material. In one embodiment, body 32 comprises a substantially radiopaque material, which enables body 32 to be visible in a radiographic image, such as an x-ray or fluoroscopic image. For example, body 32 may be constructed of stainless steel, titanium, barium sulfate ($BaSO_4$) loaded silicone or polyimide (e.g., Kapton brand polyimide film, which is available from E. I. du Pont de Nemours and Company of Wilmington, Del.). In another embodiment, body 32 comprises a substantially non-radiopaque material and distance markers 34, 36, lateral markers 40, 48, and/or centerline markers 38, 46 are formed of a radiopaque material, such that distance markers 34, 36, lateral markers 40, 48 and/or centerline markers 38, 46 are primarily visible in a radiographic image and any patient structures underlying body 32 are substantially visible in the radiographic image.

Body 32 is configured to overlay a skin surface of patient 18. In some embodiments, such as embodiments in which body 32 is comprised of silicone, body 32 is substantially flexible and substantially conforms to a contour of patient 18 when locating guide 30 is placed on the skin surface. A substantially flexible body 32 may enable body 32 to customize locating guide 30 to the contour of a particular patient 18 and/or to the particular region of patient 18 on which locating guide 30 is placed. In other embodiments, such as some embodiments in which body 32 is formed of stainless steel or titanium, body 32 may be substantially inflexible and contoured to fit over a backside of patient 16, or another surface of patient 18 near target nerve site 16. While a contour of a backside may differ substantially between patients, a contour of body 32 may be based on an average contour of a backside of, for example, adult humans. However, in some embodiments in which body 32 is formed of stainless steel or titanium, body 32 may exhibit limited flexibility if the stainless steel or titanium is thin enough. In other embodiments, body 32 may be formed of a material that is pliable enough to adapt to different skin surface contours, while at the same time, substantially hold its shape.

As shown in FIG. 2B, body 32 has a thickness $T_1$ (measured along a z-axis direction, where orthogonal x-y-z axes are shown in FIGS. 2A and 2B). In one embodiment, thickness $T_1$ is about 0.04 cm to about 1.0 cm, such as about 0.06 cm. Thickness $T_1$ may be selected to provide locating guide 30 with sufficient integrity to be handled and positioned on patient 18 with some degree of control by a clinician. If thickness $T_1$ is too small, the clinician may find it difficult to control body 32 and, accordingly, difficult to place locating guide 30 on patient 18 with accuracy and precision. On the other hand, if thickness $T_1$ is too great and body 32 is intended to be flexible, body 32 may not substantially conform to a contour of patient 18 when locating guide 30 is positioned on a skin surface of patient 18. In some cases, the suitable thickness $T_1$ of body 32 may depend upon the type of material used to form body 32. For example, if body 32 is formed of a substantially flexible material, thickness $T_1$ may be greater than when body 32 is formed of a substantially inflexible material.

An adhesive may be placed along a skin contact surface of locating guide 30 in order to couple locating guide 30 to a patient's skin at a desired position. The adhesive may be provided as a layer on one side of body 32 (e.g., an adhesive layer that includes a removable backing) or a clinician may manually apply the adhesive to locating guide 30, e.g., the adhesive may be provided in a kit with locating guide 30. In either case, the adhesive may not cover the entire skin contact surface of locating guide 30. For example, a sufficient amount of adhesive to enable locating guide 30 to remain substantially in place during the target nerve site 16 location procedure may be applied to locating guide 30. In some embodiments, the adhesive is removable and reusable, such that a clinician may attach locating guide 30 to patient 16 and subsequently adjust a position of locating guide 30 and reuse the same adhesive.

Examples of suitable adhesives include adhesives used for ground electrode pads and electrocardiogram (ECG) electrode pads, which may be, for example, tragacanth gum, karaya gum, or acrylates. The adhesive may be selected based on a preparation procedure for the medical lead 14 implantation technique. For example, the clinician may sterilize the skin surface of patient 18 near target nerve site 16 with iodine or another sterilizing agent. Locating guide 30 may be placed over the sterilized skin, and accordingly, it may be desirable for the selected adhesive to be compatible with the sterilizing agent, such that the adhesive maintains its adhesive properties when applied to the sterilized skin.

In other embodiments, other modes of attachment that enable locating guide 30 to be placed on skin of patient 18 and remain substantially in place may be used. For example, locating guide 30 may include a belt that extends around a waist of a patient or connects to a surface on which patient 18 is placed (e.g., a table or bed), or alternatively, locating guide 30 may include Velcro attachments that mate with strips already attached to patient 18. In yet another alternative embodiment, locating guide 30 may be formed of a material that exhibits a high coefficient of friction with human skin, which enables locating guide 30 to remain substantially in place when placed on skin.

Preferably, a size of locating guide 30 remains the same for all patients. Of course, if desired, a clinician may be given the option to choose from a variety of locating guides 30 having different sizes for different patients. In the embodiment shown in FIGS. 2A and 2B, width $W_1$ (measured along the x-axis direction) of locating guide 30 is about 13 centimeters (cm) to about 15 cm and length $L_1$ (measured along the y-axis direction) is about 13 cm to about 15 cm. The $L_1$ and $W_1$ values are merely one example embodiment, and in other embodiments, locating guide 30 may be any suitable size.

Figure 4:
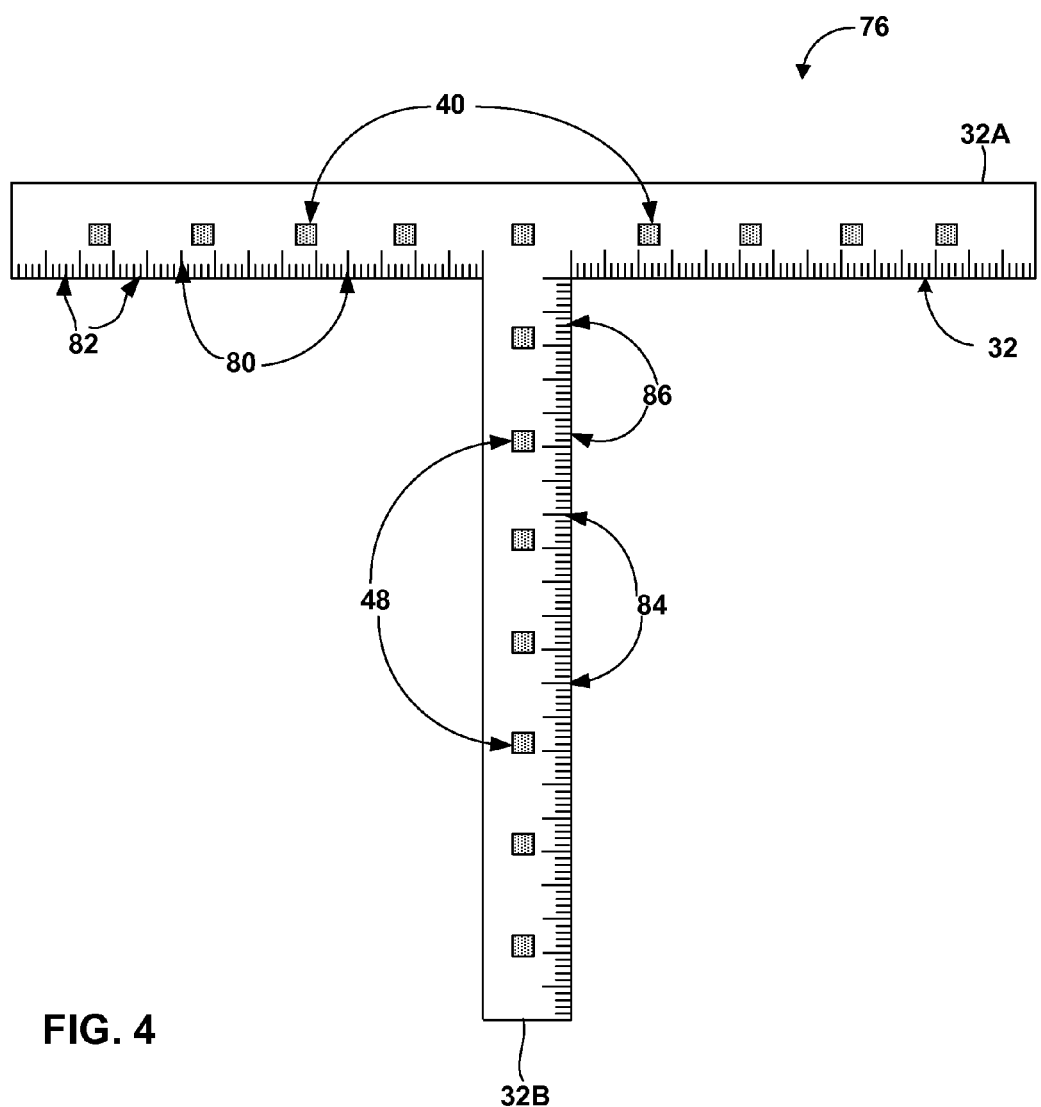
FIG. 4 illustrates a top view of another embodiment of a locating guide.

Distance reference markers 34, 36 extend from first portion 32A of body 32 ("first body portion 32A") and distance reference markers 42, 44 extend from second portion 32B of body 32 ("second body portion 32B"). While rectangular distance markers 34, 36, 42, 44 are shown in FIG. 2A, in other embodiments, distance markers 34, 36, 42, 44 may have any suitable shape, such as square, triangular, elliptical, and so forth. Furthermore, in the embodiment shown in FIGS. 2A-B, distance markers 34, 36, 42, 44 extend away from body 32. In other embodiments, distance markers 34, 36, 42, 44 may extend into body, e.g., may defined by a plurality of slots or cuts defined by body 32 that are also visible in a radiographic medical image. In addition, as shown in FIG. 4 and described below, in one embodiment, a locating guide may be substantially integral with body 32.

Distance reference markers 34, 42 may be referred to as "major markers," while distance markers 36, 44 may be referred to as "minor markers." Major markers 34, 42 are substantially evenly spaced and the respective minor markers 36, 44 are positioned between major markers 34, 42. For example, in one embodiment, major markers 34 are spaced about 1 centimeter (cm) apart, while minor markers 36 are spaced between adjacent major markers 34, such that a distance between a major marker 34 and an adjacent minor marker 36 is about 0.5 cm. However, in other embodiments, major markers 34, 42 may be spaced from the respective minor markers 36, 44 by any suitable distance and markers 34, 36 along first body portion 32A may be spaced differently than markers 42, 44. In other embodiments, locating guide 30 may include other distance reference marker configurations. For example, in one embodiment, locating guide 30 may include only one set of distance reference markers along each body portion 32A, 32B, while in another embodiment, locating guide 30 may include more than one minor marker 36, 44 between two major markers 34, 42, respectively.

In general, locating guide 30 may include labeled distance markers 34, 36, 42, 44 to indicate distance and/or provide a visual reference marker. In one embodiment, distance markers 34, 36, 42, 44 may be labeled with numbers representing units of measurement. Any suitable unit of measurement may be used, including, but not limited to, millimeters, centimeters, and inches. Alternatively, distance marks 34, 36, 42, 44 may merely be numbered consecutively, rather than representing units of measurement.

In one embodiment, distance markers 34, 36 along first body portion 32A represent x-axis coordinates and distance markers 42, 44 along second portion 32B represent y-axis coordinates. Together, distance marks 34, 36, 42, 44 define an x-y coordinate system for identifying a specific location within area of interest 49 framed by locating guide 30. An x-y coordinate system, or another type of coordinate system, may be useful for identifying a specific location within area of interest 49. A clinician may register a location within a medical image to an actual location within area of interest by matching the x-y coordinates from the image to the x-y coordinates within area of interest 49.

Centerline marker 38 are substantially aligned with along a longitudinal axis 50 of first body portion 32A and centerline markers 46 are substantially aligned with longitudinal axis 52 of second body portion 32B. In some embodiments, centerline markers 38, 46 are radiopaque. Centerline markers 38, 46 provide visual feedback to a clinician when the clinician positions locating guide 30 on patient 18. For example, the clinician may align at least one of centerline markers 38, 46 with a boney landmark of patient 18. As described in further detail below, the boney landmark may be identified via a medical image, such as a fluoroscopic image or an x-ray image, and/or the clinician may identify the relevant boney landmarks based on a physical examination of the patient. In the embodiment shown in FIG. 2A, centerline marker 38 comprises a plurality of substantially aligned openings defined by first body portion 32A and centerline markers 46 comprise a plurality of substantially aligned openings defined by second body portion 32B. Centerline markers 38, 46 defined as openings in body 32 may be visible in a radiographic image if body 32 is radiopaque because centerline markers 38, 46 may be shown in the image to be voids in the radiopaque body 32. In other embodiments, centerline markers 38, 46 may comprise one or more visible marks on the respective body portion 32A, 32B, where the markers may be radiopaque, and if body 32 is also radiopaque, centerline markers 38, 46 may have a different radiopacity than body 32. In other embodiments, locating guide 30 does not include centerline markers 38, 46, and the clinician may estimate the centerline of body portions 32A, 32B.

As shown in FIG. 2B, lateral markers 40, 48 protrude from major surface 54 of body 32. Lateral markers 40, 48 are stippled in FIGS. 2A and 2B to illustrate the protrusion from major surface 54, and the cross-hatching is not intended to limit the scope of the present invention in any way. Major surface 54 substantially lies in the plane of the image shown in FIG. 2A and extends substantially perpendicular to the plane of the image shown in FIG. 2B. That is, major surface 54 generally extends the x-y plane, where orthogonal x-y-z axes are shown in FIGS. 2A and 2B. However, major surface 54 is not necessarily planar, although in some embodiments, major surface 54 may be substantially planar. For example, in embodiments in which body 32 is formed with a predefined curvature to match a contour of patient 18, major surface 54 of body 32 may not be substantially planar. However, even if body 32 exhibits some curvature or is otherwise nonplanar, lateral markers 40, 48 may still protrude substantially away from body 32 and, may be referred to as "protruding" substantially along a z-axis direction and away from major surface 54 of body 32. Although in FIGS. 2A and 2B, lateral markers 40, 48 are substantially perpendicular to major surface 54 of body 32, in other embodiments, lateral markers 40, 48 may extend substantially perpendicular to major surface 54 of body 32. In addition, lateral markers 40, 48 may extend away from a skin surface of patient 18 when locating guide 30 is placed on the skin surface. The x-y-z axes are shown in FIGS. 2A and 2B to aid the description of locating guide 30, and are not intended to limit the present invention in any way.

Figure 8A:
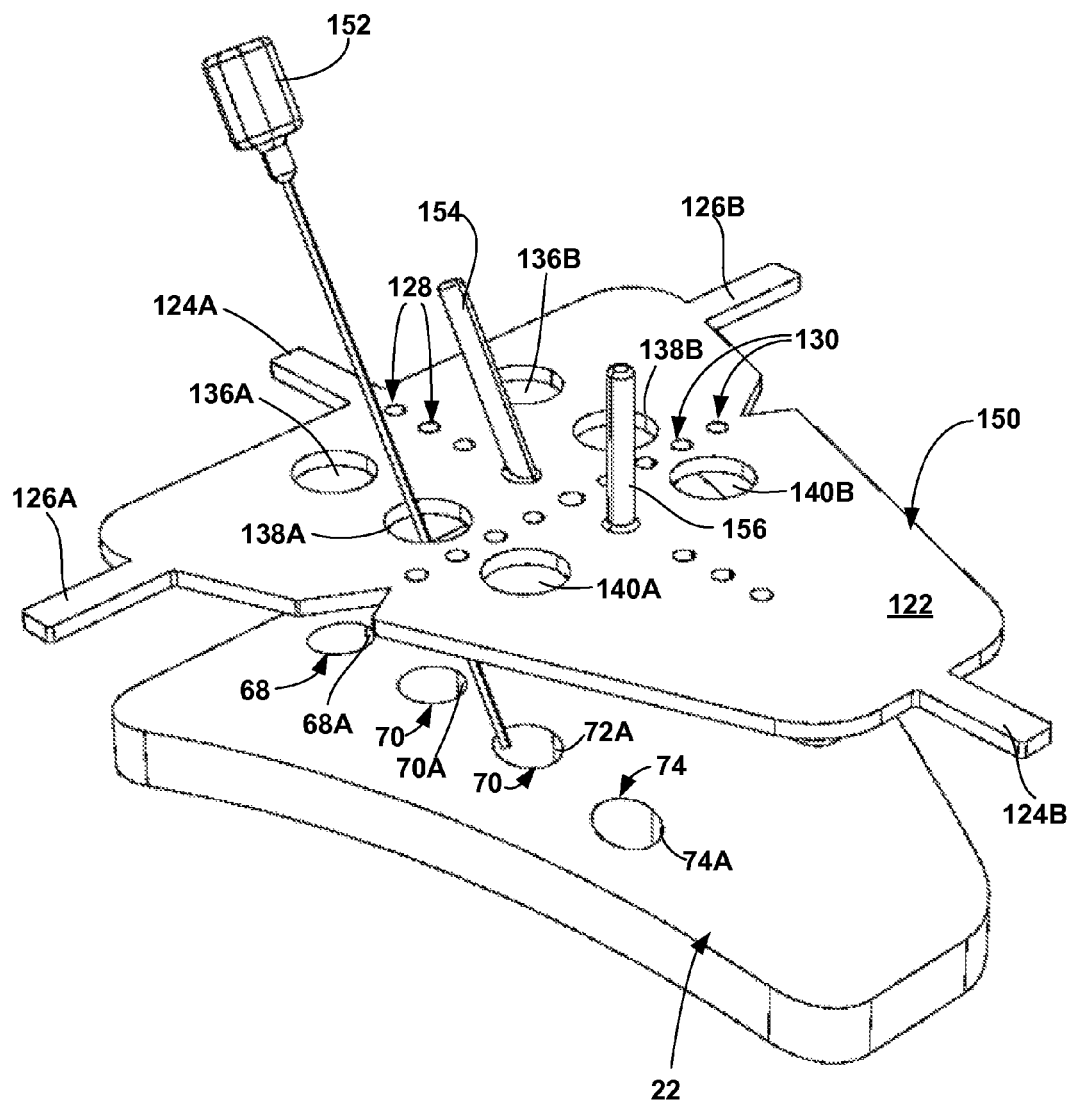
FIGS. 8A and 8B illustrate a perspective view and a side view, respectively, of a locating guide in accordance with another embodiment, where the locating guide is positioned near a schematic view of a sacrum.
Figure 8B:
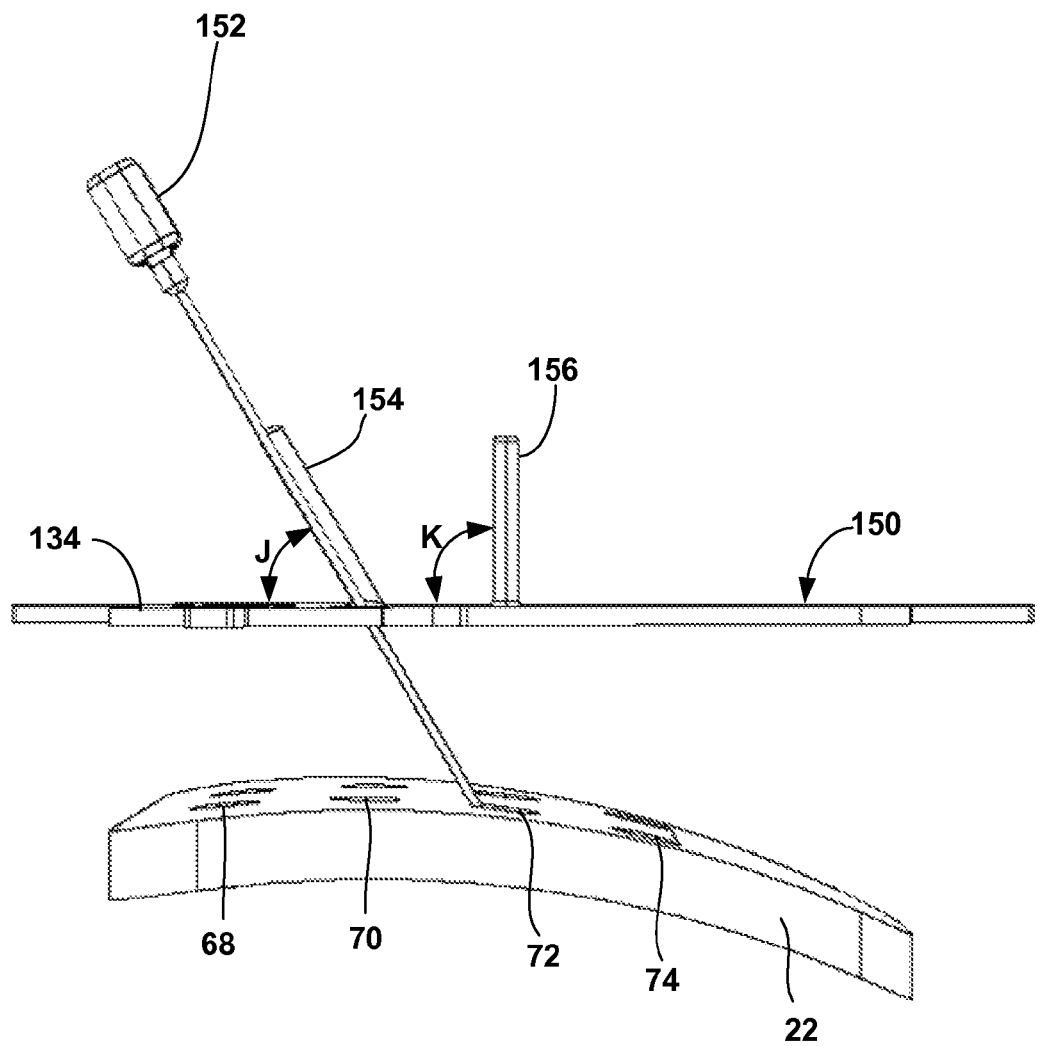

Lateral markers 40, 48 in the embodiment shown in FIGS. 2A and 2B, are spaced about 2 cm from an adjacent lateral marker. However, in other embodiments, lateral markers 40, 48 may have any suitable spacing. Lateral markers 40, 48 protrude from major surface 54 substantially the same distance in the embodiments shown in FIGS. 2A and 2B. That is, each lateral marker 40, 48 has substantially the same height (measured along the z-axis direction). In other embodiments, lateral markers 40, 48 may have different heights. In one embodiment, lateral markers 40, 48 have a height of about 0.25 cm to about 2 cm, such as about 0.5 cm to about 1 cm, although lateral markers 40, 48 may have any suitable height. Furthermore, a top surface 40A, 48A of each lateral marker does not necessarily need to be substantially parallel with major surface 54. An embodiment of a locating guide including an angled lateral marker is shown in FIGS. 8A and 8B and described below.

Lateral markers 40, 48 provide a reference point that is visible from a different perspective than distance reference markers 34, 36, 42, and 44 because lateral markers 40, 48 protrude from major surface 54 of body 32, while distance reference markers 34, 36, 42, and 44 substantially do not. In this way, locating guide 30 includes reference markers that extend in at least two dimensions. In some cases, distance reference markers 34, 36, 42, and 44 may be formed from the same material as body 32, in which case distance reference markers 34, 36, 42, and 44 may not be discernable from body 32 in a medical image, such as a fluoroscopic image. For example, if the medical image is taken from a x-axis perspective, e.g., the perspective shown in FIG. 2B, distance reference markers 34, 36, 42, and 44 may not be easily distinguishable from body 32, and in some cases, may not be distinguished from body 32. In contrast, lateral markers 40, 48 may easily be seen in the medical image taken from the x-axis perspective, even if lateral markers 40, 48 are formed of the same material as body 32, because lateral markers 40, 48 physically protrude from body 32. However, in some cases, distance reference markers 34, 36, 42, and 44 may be formed from a material having a different radiopacity than body 32 such that distance reference markers 34, 36, 42, and 44 are visible in a medical image taken from the x-axis perspective.

If the medical image is taken from a z-axis perspective, e.g., the perspective shown in FIG. 2A, distance reference markers 34, 36, 42, and 44 may be visible in the medical image, and, therefore, provide a visible reference point for the clinician to associate with the medical image. In contrast, lateral markers 40, 48 may blend in with body 32 in the medical image, and, thus, may not be visible in the medical image taken from the z-axis perspective. However, in some cases, lateral markers 40, 48 may be formed from a material having a different radiopacity than body 32 such that lateral markers 40 are visible in a medical image taken from the z-axis perspective.

In other embodiments, locating guide 30 may include other configurations of reference markers. For example, in some cases, distance markers 34, 36, 42, 44 may have a greater thickness (measured along the z-axis direction) than body 32, and therefore, protrude from body 32, distance markers 34, 36, 42, 44 may provide markers visible from at least two different perspectives. In embodiments in which distance markers 34, 36, 42, 44 protrude from body 32 in a z-axis direction, distance markers 34, 36, 42, 44 may provide two different types of reference markers, i.e., distance markers and lateral markers.

Figure 3:
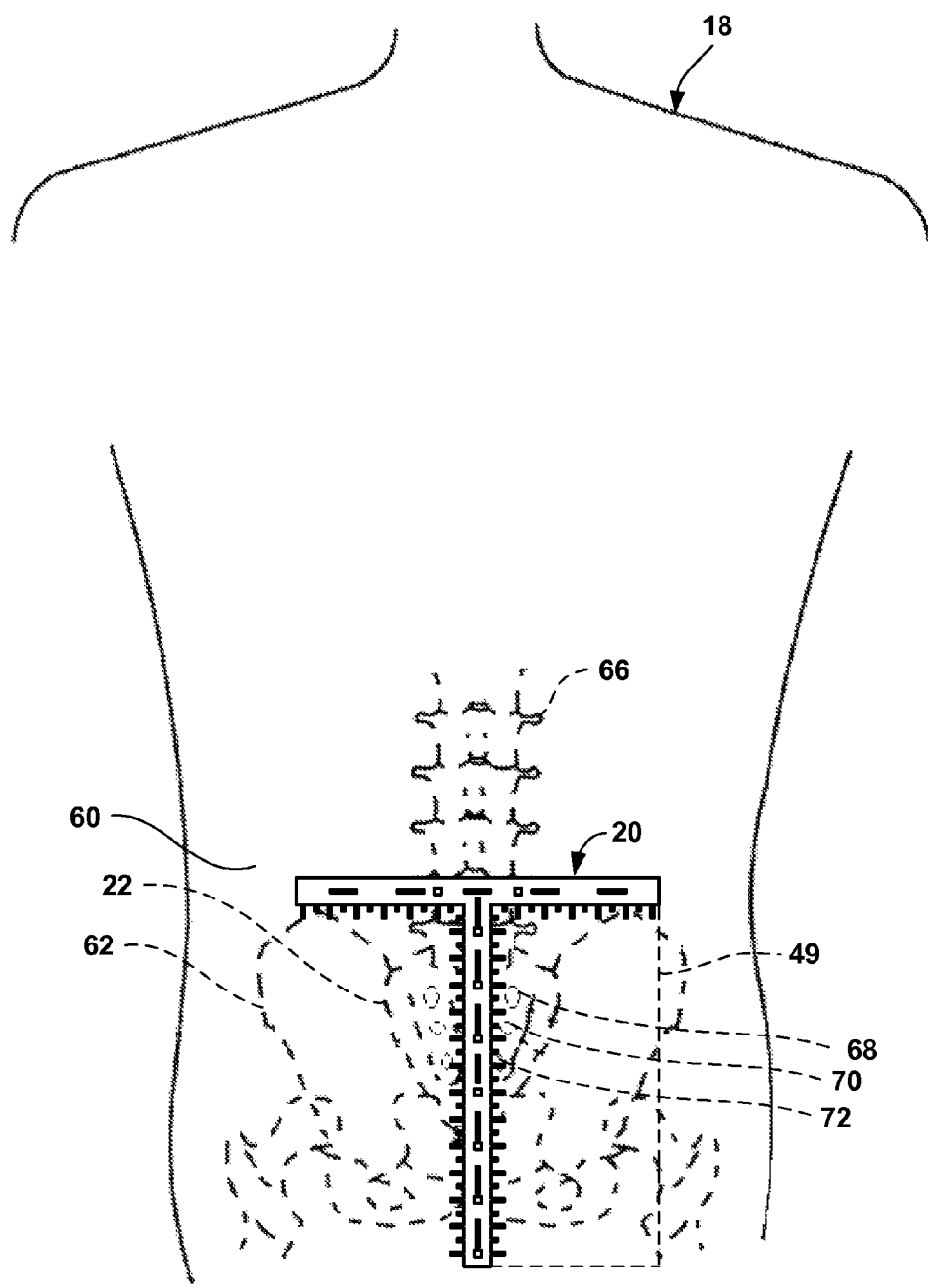
FIG. 3 illustrates the locating guide of FIGS. 2A and 2B positioned on a skin surface of a patient.

FIG. 3 illustrates one technique for identifying a location of a target sacral foramen with the aid of locating guide 30. As previously described, it may be useful to locate a sacral foramen in order to implant a medical device, such as a medical lead or a catheter, near a sacral nerve. FIG. 3 illustrates a backside of patient 18, and in particular illustrates skin 60, Ilium bone 62, sacrum 22, and a part of spinal canal 66. Ilium bone 62, sacrum 22, and spinal canal 66 are shown in phantom lines. Sacrum 22 includes S2, S3, and S4 foramen 68, 70, 72, respectively, through which the S2, S3, and S4 sacral nerves, respectively, are accessible. The S1 foramen is not shown in FIG. 3. If a clinician wishes to implant a lead or another medical element near the S3 sacral nerve, the clinician typically locates S3 foramen 70 because as previously stated, the S3 sacral nerve is accessible through S3 foramen 70. The clinician may use locating guide 30 to locate the S3 foramen 70 (or any of the other foramen of sacrum 54). While a technique for locating the S3 foramen 70 is described below, in other embodiments, locating guide 30 may be used to locate other target nerve sites within patient 18.

Preferably, locating guide 30 is positioned on a skin surface of patient 18 to frame the general area in which the S3 sacral foramen 70 is located. The clinician may use the boney landmarks of patient 18 to estimate the general location of the S3 foramen. In the present example, the boney landmarks are the posterior protuberance (or "crest") of Ilium bone 62 and/or the lower part of spinal canal 66, which runs through sacrum 22. For example, the clinician may align first portion 32A of body 32 to overlay the crest of the patient's Ilium bone 62 (i.e., where the sacroiliac ligament attaches to the Ilium) and align second portion 32B of body 32 to overlay a midline of patient 18, which may also substantially correspond to a spinal canal 66. The clinician may identify the boney landmarks with the aid of a medical image taken before or after locating guide 30 is placed on skin 60 of patient 18 and/or with the aid of a physical examination.

In one embodiment, the clinician may initially place locating guide 30 on skin surface 60 relative to Ilium bone 62 and spinal canal 66, image the patient 18 and locating guide 30, and adjust the position of locating guide if desired based on the imaged location of Ilium bone 62 and spinal canal 66 (or other relevant boney landmarks) relative to the locating guide 30. Based on the image, for example, the clinician may determine the magnitude and direction in which locating guide 30 should be moved in order to align centerline markers 38 with the crest of Ilium bone 62 and centerline markers 46 with spinal canal 66. The clinician may then reposition locating guide 30 accordingly. However, it may not be necessary to align centerline markers 38 with the crest of Ilium bone 62 and centerline markers 46 with spinal canal 66 in all cases.

It may be desirable for skin 60 to be dry and unbroken in the regions in which locating guide 30 is applied. Patient 18 may be in any position that provides the clinician access to sacrum 22. However, the prone position is preferred in some embodiments because some types of neurostimulation require testing of toe flexure, foot rotation, or a bellows response of the anus.

After locating guide 30 is attached to skin 60 of patient 18, locating guide 30 frames a general area in which a target nerve site may be located. The framed area is referred to as area of interest 49, which is outlined with phantom lines in FIG. 3. In the embodiment shown in FIG. 3, area of interest 49 frames the general area in which the S3 foramen 70 is most likely located. Of course, there may be certain patients in which area of interest 49 is inaccurate because of the patient's anatomy, in which case, the clinician may need to readjust the position of locating guide 30 if, for example, a medical image indicates the target nerve site is not located within area of interest 49. In alternate embodiments, the size and shape of locating guide 30 are adjusted to accommodate to frame an area of interest for other target nerve sites, which may affect the boney landmarks locating guide 30 overlays. The relevant boney landmarks depend upon the medical lead implantation site, which is typically dictated by the target nerve site location.

After locating guide 30 is placed on skin 60 of patient 18, the clinician may obtain a medical image of locating guide 30 and the underlying tissue proximate to locating guide 30. The clinician may use the resulting image to locate S3 sacral foramen 70. A technique for locating the S3 sacral foramen 70 or another target nerve site using locating guide 30 and a medical image of locating guide 30 and patient 18 is described in further detail below with reference to FIG. 5. After locating the S3 sacral foramen 70 in the medical image and registering the medical image to a location on the skin surface 60 of patient suitable for accessing the S3 foramen 70 with the aid of locating guide 30, the clinician may guide an introducer needle (not shown) into patient 18 near the target nerve site and guide a medical lead, catheter, or other implantable medical element through the introducer needle for implantation proximate to the S3 sacral nerve 70.

FIG. 4 illustrates a top view of locating guide 76 in accordance with another embodiment. Locating guide 76 is substantially similar to locating guide 30 of FIGS. 2A-2B, and includes body 32 defining first portion 32A and second portion 32B, major distance reference markers 80 along first body portion 32A, minor distance reference markers 82 along first body portion 32A, major distance reference markers 84 along second body portion 32B, minor distance reference markers 86 along second body portion 32B, lateral markers 40 along first body portion 32A, and lateral markers 48 along second body portion 32B. Although not shown in FIG. 4, in other embodiments, locating guide 76 may include centerline markers along first and second body portions 32A, 32B comprised of a radiopaque material, such as a radiopaque ink.

In the embodiment shown in FIG. 4, body 32 comprises a radio-transparent material, such that when a radiographic image is taken of body 32 positioned on skin 60 (FIG. 3) of patient 18, body 32 is not visible in the radiographic image and the structure underlying body 32 is visible. However, it is desirable for distance reference markers 80, 82, 84, 86, and lateral markers 40, 48 to be visible in the radiographic image in order to add useful features to the medical image that may be related back to an actual location on patient 18. Thus, distance reference markers 80, 82, 84, 86, and lateral markers 40, 48 may be formed of a radiopaque material. In one embodiment, distance markers 80, 82, 84, 86 are printed onto body 32 with a radiopaque ink, and lateral markers 40, 48 are comprised of a radiopaque material, such as silicone embedded with barium sulfate.

In some cases, it may be useful for the structure underlying body 32 to be visible, such as in cases in which locating guide 76 is inadvertently placed over the target nerve site. Body 32 may be formed of material that is relatively easily pierced by an introducer needle for implanting lead 14 in patient 18. In such cases, the clinician does not need to adjust a position of locating guide 76 relative to patient 18 to introduce lead 14 (or another medical element) into patient 18, even if body 32 overlays the target nerve site within patient 18. If locating guide 76 is purposefully or inadvertently placed over the target nerve site and body 32 is relatively easy to pierce through with an introducer needle, distance reference markers 80, 82, 84, 86 and/or lateral marker 40, 48 may be positioned relatively close to the target nerve site and the clinician may identify which distance reference markers 80, 82, 84, 86, or lateral marker 40, 48, if any, directly overlay the target nerve site. A reference marker 80, 82, 84, 86, or lateral marker 40, 48 directly overlaying the target nerve site may help the clinician implant lead 14 (FIG. 1) with improved accuracy and precision compared to a situation in which markers 80, 82, 84, 86, 40, 48 do not directly overlay a target nerve site.

Figure 5:
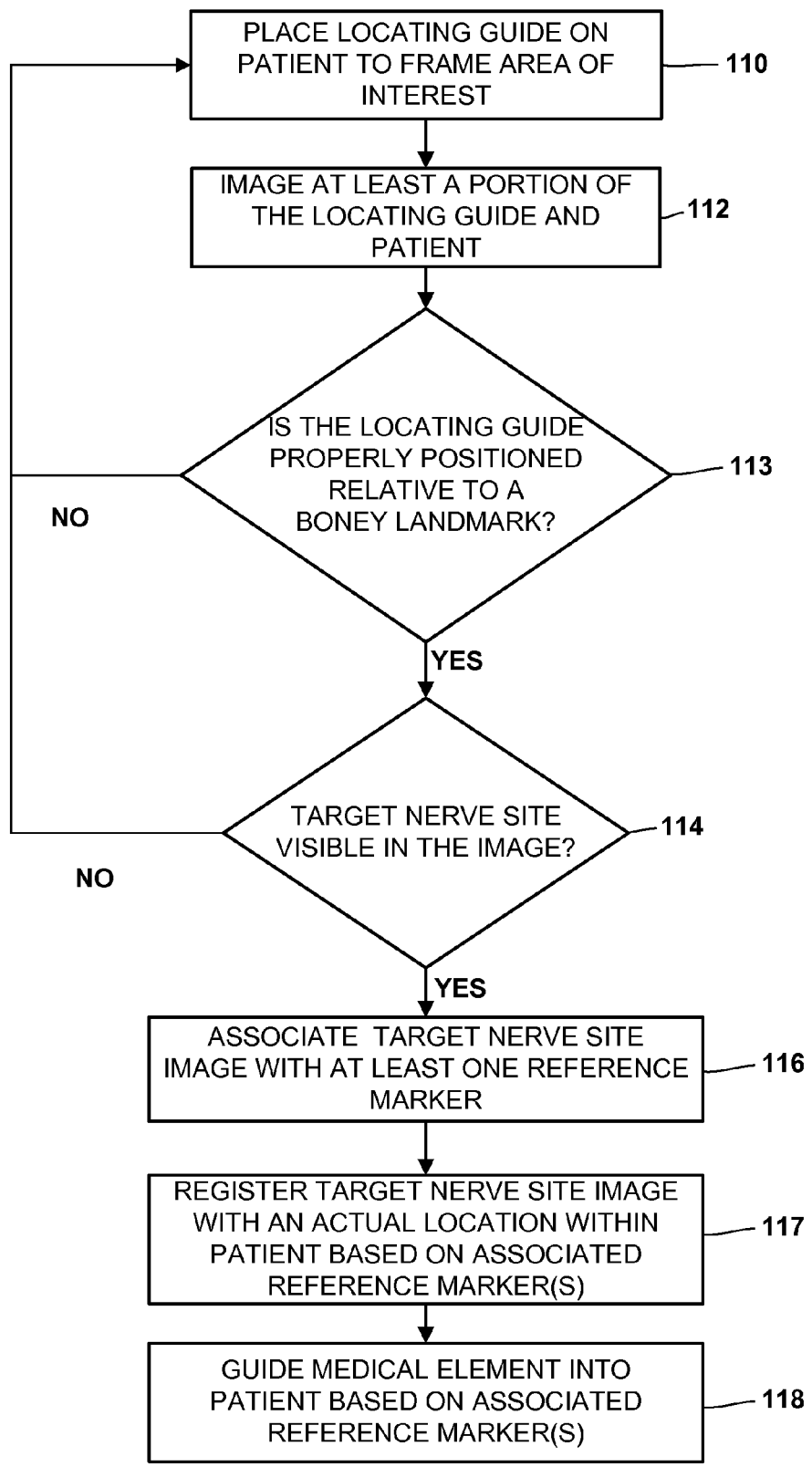
FIG. 5 is a flow diagram illustrating a technique for locating a target tissue site with the aid of the locating guide of FIGS. 2A and 2B.

FIG. 5 is a flow diagram illustrating a technique for locating a target nerve site with the aid of locating guide 30. A clinician may place locating guide 30 on patient 18 near the approximate location of target nerve site 16 (FIG. 1) to frame area of interest 49 (FIG. 2) that may provide access to target nerve site 16 (110). In one embodiment, the clinician places locating guide 30 on patient 18 relative to one or more boney landmarks. The clinician may locate the relevant boney landmarks with the aid of a medical image taken before or after locating guide 30 is placed on patient 18 and/or with the aid of a physical examination. In an alternate embodiment, the clinician may physically examine patient 18, such as by manual palpation, to locate Ilium bone 62 and spinal canal 66, and initially places first body portion 32A along the crest of Ilium bone 62 and second body portion 32B along spinal canal 66 (110).

The clinician may then obtain a medical image at least a locating guide 30 and patient 18 (112). In some embodiments, the clinician may obtain more than one image, where different images are taken from more than one perspective, such as from a lateral perspective relative to the patient (i.e., a substantially x-axis perspective of locating guide 30 when locating guide 30 is positioned proximate to sacrum 22 of patient 18) and an anterior-posterior perspective (i.e., a substantially z-axis perspective of locating guide 30 when locating guide 30 is positioned on a skin surface proximate to sacrum 22 of patient 18). The clinician may determine whether locating guide 30 is properly positioned relative to the relevant boney landmarks based on the generated image (113). If locating guide 30 is not properly positioned relative to the boney landmarks, the clinician may adjust the position of locating guide 30 on patient 18 (110) and obtain a medical image of the repositioned locating guide (112). However, it is not necessary for the clinician to do so. The clinician may instead leave locating guide 30 in place because locating guide 30 may still provide one or more visual reference markers for locating target nerve site 16 even if locating guide 30 is not positioned to overlay the desired boney landmarks.

If locating guide 30 is properly positioned relative to the boney landmarks, the clinician may determine whether target nerve site 16 is visible in the image (114). If target nerve site 16 is not visible, the clinician may reposition locating guide on patient (110). If target nerve site 16 is visible in the generated medical image, the clinician may identify target nerve site 16 within the generated medical image and associate the imaged target nerve site 16 with at least one distance reference marker 34, 36, 42, and 44 and/or lateral marker 40, 48 of locating guide 30 that is also shown in the generated medical image (116). For example, the clinician may review the medical image and identify the reference markers that are closest to target nerve site 16 and/or the relative location of target nerve site 16 and at least one of the reference markers of locating guide 30. As another example, the distance markers 34, 36, 42, and/or 44 shown in the image may also indicate a distance of the target tissue site relative to a portion of locating guide 30.

As previously described, if the medical image is taken from the z-axis perspective relative to the general plane of the patient's back, at least some of distance reference marker 34, 36, 42, and 44 are visible in the medical image. In some cases, such as when lateral markers 40, 48 are formed of a material having a different radiopacity than body 32, at least some of lateral markers 40, 48 may also be visible in the medical image taken from the z-axis perspective. If the medical image is taken from the x-axis perspective, at least some of lateral markers 40, 48 are visible in the medical image. In some cases, such as when distance reference marker 34, 36, 42, and 44 are formed of a material having a different radiopacity than body 32, at least some of distance reference marker 34, 36, 42, and 44 may also be visible in the medical image taken from the x-axis perspective. Locating guide 30 that include reference markers in at least two different dimensions or planes increases the visibility of reference markers in the medical image, regardless of the angle the image is taken from.

After associating the imaged target nerve site 16 with at least one imaged marker (116), the clinician may register the medical image of target nerve site 16 and locating guide 30 with an actual location on patient 18 based on the one or more associated reference markers (117). That is, the clinician may align the medical image of target nerve site 16 and locating guide 30 with an actual location on or within patient 18 using at least one of the reference markers of locating guide 30. When "registering" the image to an actual location on patient 18, the clinician may use the relative position between locating guide 30, which is placed on patient 18, and the position of locating guide 30 (and any of its reference markers) in the image to locate the actual target nerve site 16.

Registering the medical image to an actual location at patient 18 may help the clinician interpret the medical image (e.g., what angle the medical image is taken from, what scale, etc.) and approximate an actual location of target nerve site 16. In particular, the clinician may approximate an actual location of target nerve site 16 based on the actual location of the reference markers associated with the target nerve site 16. If desired, the clinician may implant a medical element proximate to target nerve site 16 within patient 18 based on the approximated location of target nerve site 16 (118). For example, the clinician may guide a distal end of an introducer needle to target nerve site 16 using the reference marker(s) associated with target nerve site 16 as a guide. Locating guide 30 may remain on patient 18 as the clinician guides the introducer needle to target nerve site 18 to provide a substantially stable reference point that is also visible in the medical image.

In some cases, the clinician may not be able to guide the introducer needle to target nerve site 16 despite the use of locating guide 30. For example, the clinician may misread the reference markers in the generated image or incorrectly associate the target nerve site 16 with at least one reference marker. Using S3 foramen 70 (FIG. 3) as an example, if the clinician does not locate the S3 foramen 70 and cannot introduce the distal end of the introducer needle through the S3 foramen 70, the clinician may leave the needle within patient 18, obtain another medical image of locating guide 30, tissue of patient 18 proximate to locating guide 30, and the needle, which is typically radiopaque. The clinician may register the location of the needle shown in the image with the actual location of the needle with the aid of locating guide 30. The clinician may then reguide the needle toward foramen 70 with the aid of the image and locating guide 30. Thus, in some embodiments, both an introducer needle and guide 30 may provide external reference points for identifying the location of S3 foramen 70.

Once the introducer needle is introduced into the S3 foramen 70, lead 14 (FIG. 1) may be inserted into patient 18 through the introducer needle and implanted proximate to the S3 sacral nerve. The exact location of the S3 sacral nerve may be determined by testing the patient's responses to electrical stimulation that is delivered through lead 14, e.g., from an external stimulator that is coupled to a proximal end of the lead.

Figure 6A:
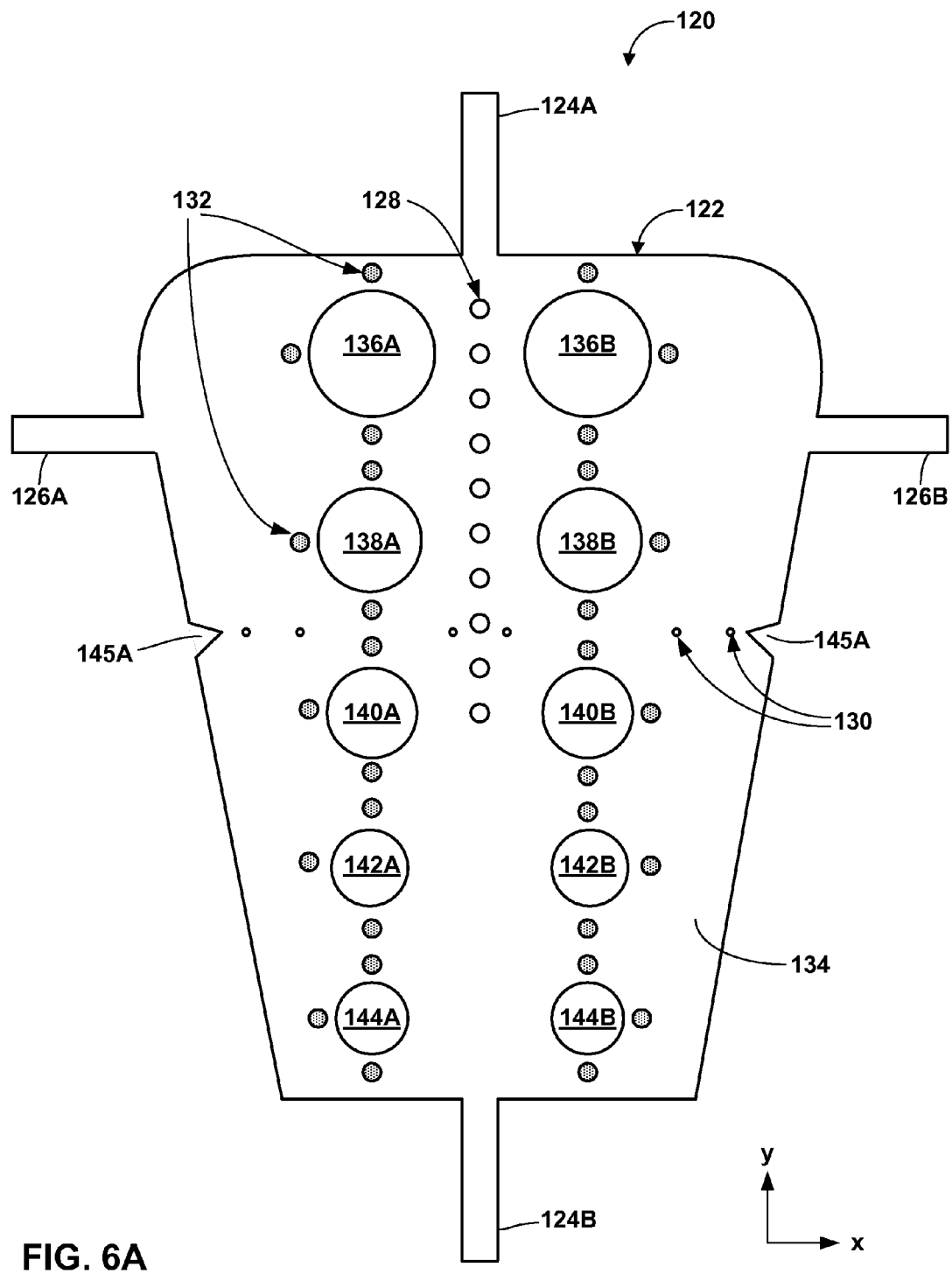
FIGS. 6A and 6B illustrate a plan and a side view, respectively, of a locating guide in accordance with another embodiment.
Figure 6B:
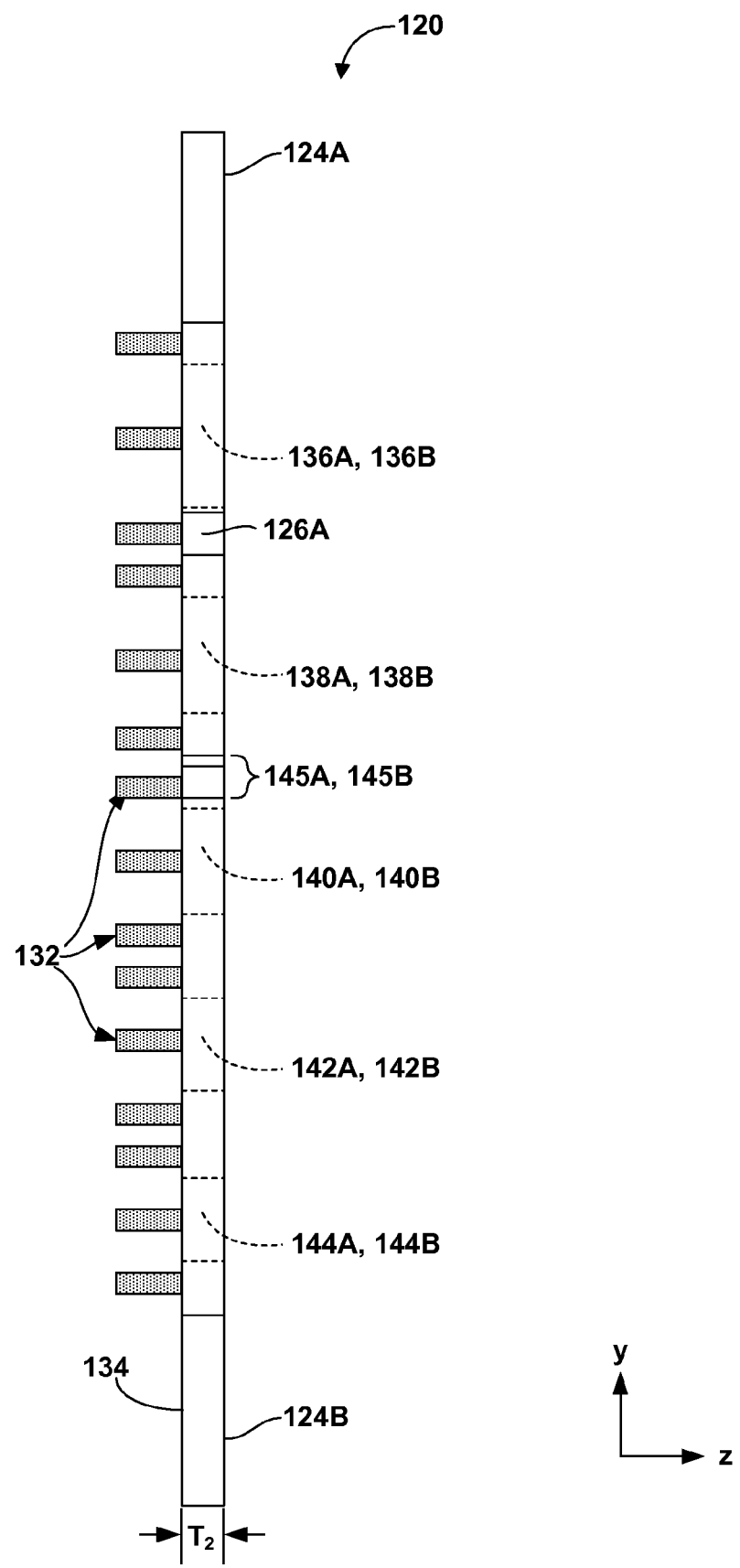

FIGS. 6A and 6B illustrate a top and a side view, respectively, of locating guide 120 in accordance with another embodiment of the invention. Locating guide 120 provides a stationary reference point for identifying a target nerve site for implantation of a medical element. Just as with locating guide 30, locating guide 120 may be placed on a patient's skin surface to provide one or more externally visible reference markers that are also visible in a medical image (e.g., a fluoroscopic image). Locating guide 120 may be coupled to a patient's skin using any suitable mechanism, such as the ones described above with reference to locating guide 30.

Locating guide 120 includes body 122, which is approximates the shape of sacrum 22 (FIG. 3). In the embodiment shown in FIGS. 6A and 6B, body 122 is shaped to resemble an orthographic projection of sacrum 22. Body 122 may be formed of a material similar to body 32. Locating guide 120 further includes reference markers 124A, 124B, which are substantially aligned along the y-axis direction (orthogonal x-y-z axes are shown in FIGS. 6A and 6B), reference markers 126A, 126B, which are substantially aligned along the x-axis direction, centerline reference markers 128, 130, and lateral reference markers 132. Reference markers 124A, 124B, 126A, 126B, 128, 130, and 132 may each be integrally formed with body 122 (e.g., molded, casted, extruded, stamped or punched from body 122, printed onto body 122, etc.) or fixed to body 122 (e.g., via an adhesive, ultrasonic welding, or otherwise).

Lateral reference markers 132 are stippled in FIGS. 6A and 6B to illustrate the protrusion in the z-axis direction from body 122, and the cross-hatching is not intended to limit the scope of the present invention in any way. In FIGS. 6A and 6B, lateral markers 132 protrude from major surface 134 of body 122. Major surface 134 substantially lies in the plane of the image shown in FIG. 6A and extends substantially perpendicular to the plane of the image shown in FIG. 6B. That is, major surface 134 generally extends along the x-y plane, where orthogonal x-y-z axes are shown in FIGS. 6A and 6B. However, major surface 134 is not necessarily planar, although in some embodiments, major surface 134 may be substantially planar. The x-y-z axes are shown in FIGS. 6A and 6B to aid the description of locating guide 30, and are not intended to limit the present invention in any way.

Centerline reference markers 128, 130 are similar to centerline markers 38, 46 of locating guide 30, and provide a reference point for positioning locating guide 120 on patient 18, and may also help register a medical image with an actual location on patient 18. In the embodiment shown in FIGS. 6A and 6B, centerline markers 128, 130 designate a center of locating guide 120 along both the x-axis direction and y-axis direction. Centerline markers 128, 130 are visible in both a radiographic image and to the clinician's eye without the aid of an imaging device. While centerline markers 128, 130 are shown to be apertures in body 122, in other embodiments, such as in embodiments in which body 122 is formed of a radio-transparent material, centerline markers 128, 130 may be formed of a radiopaque material, such as radiopaque ink printed on body 122. Furthermore, in some embodiments, locating guide 120 does not include centerline markers 128 and/or 130.

As shown in FIG. 6B, body 122 has a thickness $T_2$ (measured along a z-axis direction). In one embodiment, thickness $T_2$ is about 0.04 cm to about 1.0 cm, such as about 0.06 cm. In general, thickness $T_2$ may be selected to provide locating guide 120 with sufficient integrity to be handled and positioned on patient 18 with some degree of control by a clinician. Body 122 defines S-I junction markers 145A and 145B. A sacral-iliac (S-I) junction is the region in which the Ilium bone 62 (FIG. 3) meets the sacrum 22. S-I junction markers 145A and 145B provide another reference point that a clinician may use to align locating guide 120 with a patient's sacrum. In other embodiments, S-I junction markers 145A and 145B may extend from body 122, rather than being defined by a cut-out in body 122.

Body 122 defines foramen apertures 136A-B, 138A-B, 140A-B, 142A-B, and 144A-B. Foramen apertures 136A-B, 138A-B, 140A-B, 142A-B, and 144A-B provide openings in body 122 through which the clinician may introduce an introducer needle to implant a medical element into patient 18 proximate to target nerve site 16 (FIG. 1). Foramen apertures 136A, 138A, 140A, 142A, and 144A are configured to be located on an opposite side of a midline of patient 18 from foramen apertures 136B, 128B, 140B, 142B, and 144B when locating guide 120 is placed on patient 18 such that reference markers 124A, B are substantially aligned with spinal canal 66 (FIG. 3) of patient 18.

A plurality of foramen apertures 136A-B, 138A-B, 140A-B, 142A-B, and 144A-B enable a clinician to implant medical elements into more than one foramen at a time without having to adjust a position of locating guide 120. For example, at least one set of apertures may be configured to substantially align with S4 sacral foramen 68 (FIG. 3) when locating guide 120 is positioned over sacrum 22 (FIG. 3), while another set of apertures may substantially align with S3 sacral foramen 70 (FIG. 3), and another set of apertures may substantially align with S2 sacral foramen 72. The particular apertures 136A-B, 138A-B, 140A-B, 142A-B, and 144A-B that correspond to sacral foramen 68, 70, 72 may differ, depending upon the size of sacrum 22 (FIG. 2) of patient 18. For example, in one patient, apertures 136A, B may correspond to the S4 sacral foramen 68, while in another patient, apertures 138A, B may correspond to the S4 sacral foramen.

In embodiments in which foramen apertures 136A-B, 138A-B, 140A-B, 142A-B, and 144A-B are configured to substantially align with sacral foramen (e.g., based on the average distance between foramen), foramen apertures 136A-B, 138A-B, 140A-B, 142A-B, and 144A-B may also provide general guidance to a clinician when implanting a medical element into patient 18. If apertures 138A, 138B are configured to align with the S3 sacral foramen 70, for example, the clinician may introduce a medical element through apertures 138A, 138B in order to access the S3 sacral foramen 70.

Figure 7:
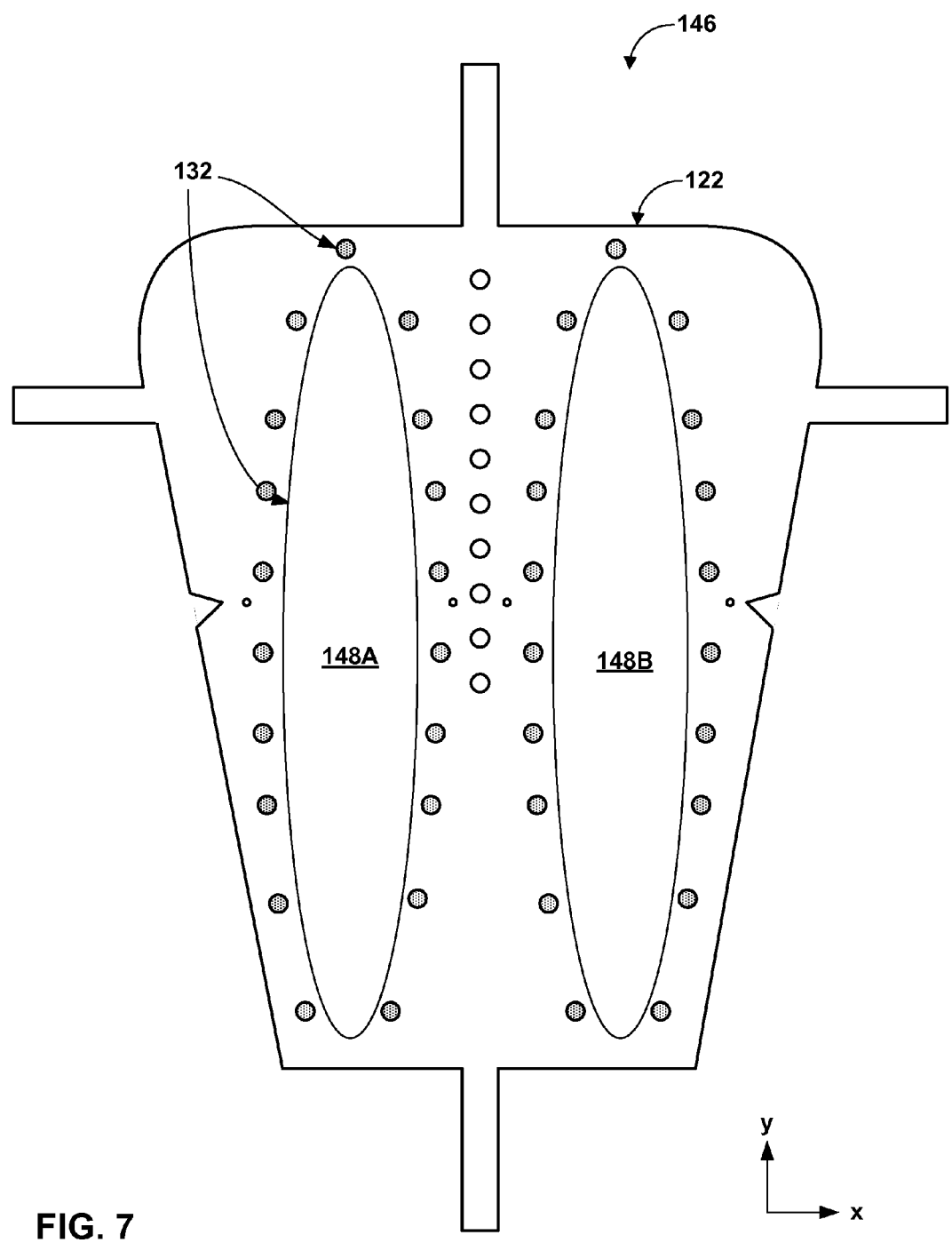
FIG. 7 illustrates a top view of a locating guide in accordance with another embodiment.

Although five sets of circular foramen apertures 136A-B, 138A-B, 140A-B, 142A-B, and 144A-B are shown in FIG. 6A, in other embodiments, locating guide 120 may include any suitable number of foramen apertures having any suitable shape. For example, as shown in FIG. 7, locating guide 146 may include two substantially elliptical apertures 148A and 148B instead of a plurality of circular apertures 136A-B, 138A-B, 140A-B, 142A-B, and 144A-B. Elliptical apertures 148A, 148B are surrounded by lateral markers 132 that extend in a z-axis direction away from body 122. Lateral markers 132 are arranged in a substantially curved pattern around elliptical apertures 148A, 148B. In other embodiments, lateral markers 132 may have another arrangement relative to elliptical apertures 148A, 148B. In other aspects, locating guide 146 is substantially similar to locating guide 120. Alternatively, a locating guide may include three sets of substantially circular apertures, where each set corresponds to one of the S4, S3, and S2 sacral foramen 68, 70, 72, as shown in FIGS. 8A and 8B and described below.

In embodiments in which body 122 is comprised of a radiopaque material, foramen apertures 136A-B, 138A-B, 140A-B, 142A-B, and 144A-B further provide reference points that are visible in a radiographic medical image. In other embodiments, foramen apertures 136A-B, 138A-B, 140A-B, 142A-B, and 144A-B may not be apertures defined by body 122, but may be, for example, formed of a different material than body 122 that is radiopaque or has a different level of radiopacity than body 122 and/or outlined by a radiopaque and visible material (e.g., a radiopaque ink). In embodiments in which foramen apertures 136A-B, 138A-B, 140A-B, 142A-B, and 144A-B are covered by material, it may be desirable for the material to be configured such that an introducer needle may puncture directly through the material to reach target nerve site 16 within patient 18.

In the embodiment shown in FIGS. 6A-6B, reference markers 124A, B and 126A, B extend substantially along a major surface 134 of body 122, i.e., do not protrude significantly from body 122 in a z-axis direction. A clinician may align locating guide 120 relative to a sacrum 22 of patient 18 with the aid of reference markers 124A, B and 126A, B. In particular, reference markers 124A, B and 126A, B are configured to overlay a crest of Ilium bone 62 and spinal canal 66 (FIG. 3), respectively. Just as with locating guide 30 of FIGS. 2A-2B, a size of locating guide 120 may remain the same for all patients. In some embodiments, however, a clinician may be given the option to choose from a variety of locating guides 120 having different sizes for different patients.

Lateral reference markers 132 are similar to lateral markers 40, 48 of locating guide 30. Lateral reference markers 132 provide reference points that are visible from a perspective that reference markers 124A, B and 126A, B, centerline reference markers 128, 130, and foramen apertures 136A-B, 138A-B, 140A-B, 142A-B, and 144A-B may not be visible from. In this way, lateral markers 132, reference markers 124A, B and 126A, B, centerline reference markers 128, 130, and foramen apertures 136A-B, 138A-B, 140A-B, 142A-B, and 144A-B provide reference points that extend in more than one dimension.

In the embodiment shown in FIGS. 6A-6B, lateral markers 132 surround each foramen aperture 136A-B, 138A-B, 140A-B, 142A-B, and 144A-B. In particular, three lateral markers 132 surround each foramen aperture 136A-B, 138A-B, 140A-B, 142A-B, and 144A-B such that a center point between the three lateral markers 132 also indicate a center of the respective foramen aperture 136A-B, 138A-B, 140A-B, 142A-B, and 144A-B. The clinician may estimate a center of each foramen aperture 136A-B, 138A-B, 140A-B, 142A-B, and 144A-B based on a location of lateral markers 132.

Other arrangements of lateral markers 132 are also contemplated, as long as lateral markers 132 provide some guidance to a clinician when registering a medical image of locating guide 120 and tissue of patient 18 to an actual location on patient 18. For example, in other embodiments, a single lateral marker 132 may be placed relative to each foramen aperture 136A-B, 138A-B, 140A-B, 142A-B, and 144A-B, or lateral markers 132 may be placed independently of foramen apertures 136A-B, 138A-B, 140A-B, 142A-B, and 144A-B.

Figure 6C:
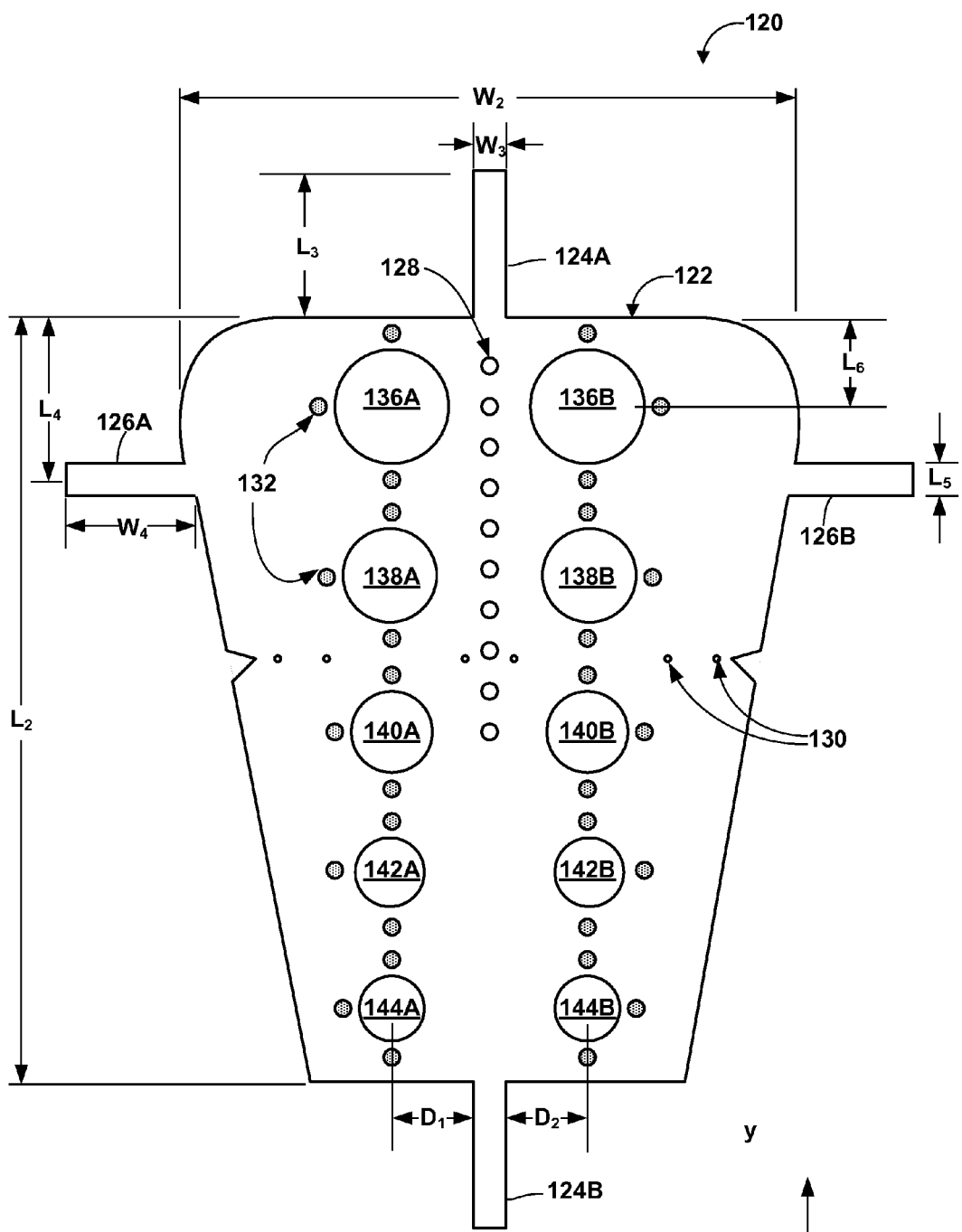
FIG. 6C illustrates an embodiment of various dimensions of the locating guide of FIGS. 6A and 6B.

FIG. 6C illustrates locating guide 120 and one embodiment of the dimensions of locating guide 120. The dimensions provided below with reference to FIG. 6C are merely one embodiment, and in other embodiments, locating guide 120 may have any suitable dimensions. The overall length $L_2$ (measured along the y-axis direction) and width $W_2$ (measured along the x-axis direction) of body 122 of locating guide 120 is based on the size of a human adult sacrum. While the relative size of a human adult sacrum may differ between each patient, locating guide 120 may be representative of an average size of a human adult sacrum. In the embodiment of locating guide 120 shown in FIG. 6C, length $L_2$ of body 122 is about 15 cm to about 18 cm, such as about 16.5 cm (about 5.9 inches to about 7.0 inches, such as about 6.5 inches), and width $W_2$ of body 122 is about 14 cm to about 16 cm, such as about 15.24 cm (about 5.5 inches to about 6.3 inches, such as about 4.0 inches).

Markers 124A, 124B may extend from body 122 at any suitable length $L_3$ that is selected to provide a clinician with sufficient markers 124A, 124B with a center of sacrum 22. In the embodiment shown in FIG. 6C, length $L_3$ is about 1.5 cm to about 3.5 cm, such as about 2.54 cm (0.59 inches to about 1.38 inches, such as about 1.0 inches). Markers 124A, 124B each have a width $W_3$ of about 0.5 cm to about 0.8 cm, such as about 0.635 cm (about 0.05 inches to about 0.35 inches, such as about 0.25 inches). Similarly, markers 126A, 126B extend from body 122 at any suitable width $W_4$, which is selected to provide a clinician with sufficient markers 126A, 126B with a crest of Ilium bone 62 (FIG. 3). In the embodiment shown in FIG. 6C, width $W_4$ is about 1.0 cm to about 4.0 cm, such as about 2.54 cm (0.04 inches to about 1.5 inches, such as about 1.0 inch). A center of each markers 126A, 126B is distanced from an edge of body 122 by distance $L_4$, which may be 1.0 cm to about 4.0 cm, such as about 2.54 cm (0.04 inches to about 1.5 inches, such as about 1.0 inch). Markers 126A, 126B each have a length $L_5$ of 0.4 cm to about 1.27 cm, such as about 0.635 cm (about 0.15 inches to about 0.5 inches, such as about 0.25 inches).

Each lateral marker 132 has a diameter of about 0.0127 cm to about 0.4 cm, such as about 0.254 cm (about 0.05 inches to about 0.15 inches, such as about 0.10 inches). In other embodiments, however, lateral marker 132 may have a shape other than a circle. Sacral foramen apertures 136A, 136B each have a diameter of about 1.27 cm to about 1.78 cm, such as about 1.5 cm (about 0.50 inches to about 0.70 inches, such as about 0.60 inches), and do not necessarily have the same diameter. Sacral foramen apertures 138A, 136B each have a diameter of about 1.14 cm to about 1.65 cm, such as about 1.4 cm (about 0.45 inches to about 0.65 inches, such as about 0.55 inches), and do not necessarily have the same diameter. Sacral foramen apertures 140A, 140B each have a diameter of about 1.0 cm to about 1.5 cm, such as about 1.27 cm (about 0.40 inches to about 0.60 inches, such as about 0.50 inches), and do not necessarily have the same diameter. Sacral foramen apertures 142A, 142B each have a diameter of about 0.95 cm to about 1.46 cm, such as about 1.21 cm (about 0.375 inches to about 0.575 inches, such as about 0.475 inches), and do not necessarily have the same diameter. Sacral foramen apertures 144A and 144B each have a diameter of about 0.90 cm to about 1.40 cm, such as about 1.14 cm (about 0.35 inches to about 0.55 inches, such as about 0.45 inches), and do not necessarily have the same diameter.

The distances between each sacral foramen may differ based on the patient, thus, a distance between a center of foramen apertures 136A, 136B and 138A, 136B, respectively, a distance $D_2$ between apertures 138A, 138B and 140A, 140B, respectively, a distance between apertures 140A, 140B and 142A, 142B, respectively, and a distance between apertures 142A, 142B and 144A, 144B, respectively may not accurately represent the distances between a particular patient's foramen. However, the distances between adjacent foramen apertures may be generic enough to match a large range of patients. For example, if apertures 136A, B are configured to substantially align with S4 foramen 68 (on opposite sides of spinal canal 66), apertures 138A, B are configured to substantially align with S3 foramen 70 (on opposite sides of spinal canal 66), a distance between a center of apertures 136A, B and a center of an adjacent aperture 138A, B may be calculated based on the average distance between an adult human's S1 and S2 sacral foramina.

Based on one measurement of the average distance between an adult human's sacral foramina, the distance between a center of apertures 136A, B and a center of an adjacent aperture 138A, B is about 1.9 cm to about 3.175 cm, such as about 2.6 cm (about 0.75 inches to about 1.25 inches, such as about 1.024 inches), the distance between a center of apertures 138A, B and a center of an adjacent aperture 140A, B is about 1.65 cm to about 2.92 cm, such as about 2.30 cm (about 0.65 inches to about 1.15 inches, such as about 0.906 inches), the distance between a center of apertures 140A, B and a center of an adjacent aperture 142A, B is about 1.27 cm to about 2.86 cm, such as about 1.8 cm (about 0.50 inches to about 0.90 inches, such as about 0.709 inches), and a distance between a center of apertures 142A, B and a center of an adjacent aperture 144A, B is about 1.0 cm to about 2.0 cm, such as about 1.5 cm (about 0.40 inches to about 0.80 inches, such as about 0.591 inches). In the embodiment shown in FIG. 6C, the center of each aperture 136A, B is located length $L_6$ from an edge of body 122. In one embodiment, length $L_6$ is about 1.27 cm to about 2.54 cm, such as about 1.90 cm (about 0.50 inches to about 1.0 inches, such as about 0.75 inches).

FIGS. 8A and 8B are perspective and side views, respectively, of locating guide 150 in accordance with another embodiment. Also shown in FIGS. 8A and 8B is a schematic view of sacrum 22, including the S2 foramen 68, S3 foramen 70, S4 foramen 72, and S5 foramen 74, and introducer needle 152. Sacrum 22 includes a set of the S2-S5 foramen 68, 70, 72, and 74 on opposite sides of a midline of patient 18. The illustration of sacrum 22 in FIGS. 8A and 8B is greatly simplified for purposes of illustration, and is not intended to be limiting in any way.

Locating guide 150 is substantially similar to locating guide 120 of FIGS. 6A and 6B, and includes body 122, reference markers 124A-B, 126A-B, and midline reference markers 128, 130. However, locating guide 150 includes three sets of foramen apertures 136A-138B, 138A-138B, and 140A-140B, rather than five sets, as locating guide 120 included. In addition, rather than including a plurality of lateral markers 132 positioned around each foramen aperture, locating guide 150 includes lateral markers 154 and 156. Lateral marker 154 is positioned between sacral foramen aperture 138A and 138B, and lateral marker 156 is positioned between sacral foramen apertures 140A and 140B. In alternate embodiments, however, lateral markers 154 and 156 are not between foramen apertures 138A-B and 140A-B, respectively, and may be placed at any suitable location on body 122. In the embodiment shown in FIGS. 8A and 8B, lateral markers 154 and 156 are substantially aligned with midline reference markers 128. However, in other embodiments, lateral markers 154 and 156 may be placed at any suitable location on body 122.

As previously described, sacrum 22 is curved relative to a skin surface 60 (FIG. 3) of patient 18, and each foramen 68, 70, 72, and 74 may also include walls 68A, 70A, 72A, and 74A, respectively, that are angled relative to skin surface 60. In order to guide introducer needle 152 through a foramen 68, 70, 72 or 74 to reach a respective sacral nerve, the clinician may need to orient introducer needle 152 through the respective foramen at an angle relative to the skin surface 60. The angle may be selected to be substantially compatible with the curved walls of the particular foramen. For example, as shown in FIG. 8B, in order to introduce needle 152 into the S3 foramen 72, it may be desirable to orient needle 152 at around angle J or an angle similar to angle J relative to major surface 134 of body 122 of locating guide 150. In some embodiments, angle J is about 45 degrees to about 75 degrees, such as about 60 degrees, although the angle may differ between patients.

As shown in FIG. 8B, lateral marker 154 extends from major surface 134 of body 122 at an angle J. When introducing needle 152 into S3 foramen 72, the clinician may orient needle 152 to substantially match the orientation of lateral marker 154 in order to access S3 foramen 72 through apertures 138A and 138B (or another aperture). In this way, lateral marker 154 provides a visual guide that indicates an introduction angle for introducer needle 152. Positioning lateral marker 154 near foramen apertures 138A and 138B may also suggest to the clinician that needle 152 may be introduced into apertures 138A and 138B at the angle denoted by lateral marker 154 in order to access the S3 foramen 72 (or another sacral foramen). Foramen apertures 138A-138B may be positioned on locating guide 150 such that when reference markers 124A-124B are substantially aligned with spinal canal 66 (FIG. 3) and reference markers 126A-126B are substantially aligned with a crest of Ilium bone 62, a clinician may introducer needle 152 into apertures 138A and 138B at angle J and reach the S3 foramen 70. However, because anatomy may differ between patients, apertures 138A-138B may not be aligned with the S3 foramen 70 for all patients.

Lateral marker 156 may also provide a visual guide that indicates an introduction angle at which introducer needle 152 may be introduced into foramen apertures 140A and 140B of locating guide 150. Lateral marker 156 extends from major surface 134 of body 122 at an angle K. Needle 152 may be oriented at an angle of about 80 to about 100 degrees, such as about 90 degrees, relative to major surface 134 of locating guide 150 in order to guide needle 152 through S4 foramen 72. Accordingly, angle K may be about 80 degrees to about 100 degrees. Foramen apertures 140A-140B may be positioned on locating guide 150 such that when reference markers 124A-124B are substantially aligned with spinal canal 66 (FIG. 3) and reference markers 126A-126B are substantially aligned with a crest of Ilium bone 62, a clinician may introducer needle 152 into apertures 140A and 140B at angle J and reach the S4 foramen 72. However, because anatomy may differ between patients, apertures 140A-140B may not necessarily be aligned the S4 foramen 72 for all patients.

In other embodiments, locating guide 150 may include other lateral reference markers that are oriented at an angle relative to major surface 134 of body 122, where the angle may be selected to provide guidance to a clinician when the clinician introduces needle 152 or another device into a particular sacral foramen. In some embodiments, the lateral reference markers may extend from major surface 134 of body at an angle of about 45 degrees to about 100 degrees.

Figure 9:
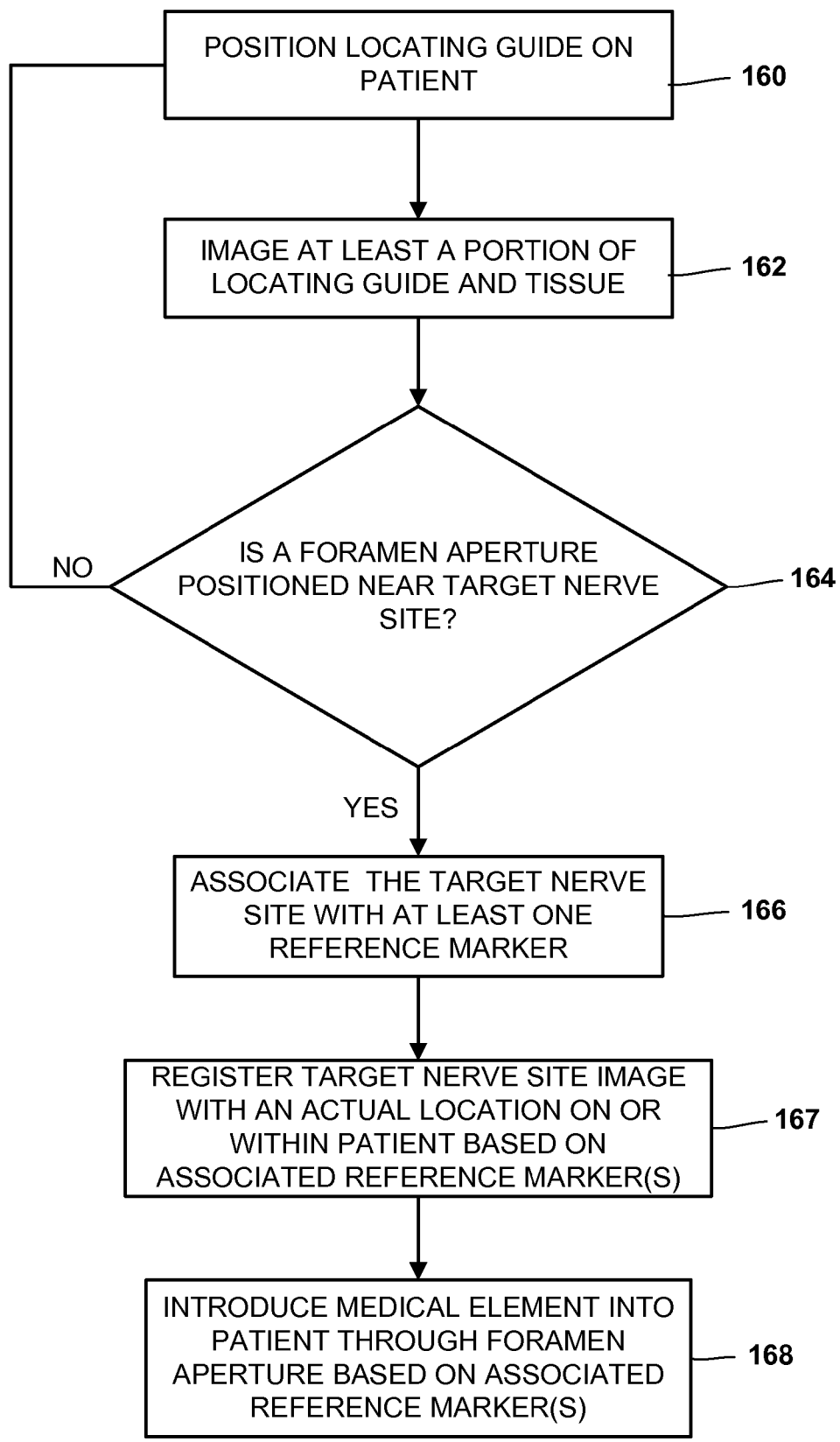
FIG. 9 is a flow diagram illustrating a technique for locating a target tissue site with the aid of the locating guide of FIGS. 6A and 6B.

A clinician may employ the technique shown in FIG. 5 to locate a target nerve site 16 with the aid of locating guide 120. FIG. 9 is a flow diagram of another technique that a clinician may use to locate a target nerve site with any of locating guides 120, 146, and 150. Locating guide 120 is primarily referred to throughout the description of FIG. 9 for ease of description. The clinician may position locating guide 120 on a skin surface of patient 18 near an approximate location for accessing target nerve site 16 (FIG. 1) (160). In one embodiment, the clinician places locating guide 120 on patient 18 relative to one or more boney landmarks. The clinician may locate the relevant boney landmarks with the aid of a medical image taken before or after locating guide 120 is placed on patient 18 and/or with the aid of a physical examination. For example, in the embodiment shown in FIG. 9, the clinician physically examines patient 18 to locate Ilium bone 62 and spinal canal 66, and initially aligns reference markers 126A, B with the crest of Ilium bone 62 and reference markers 124A, B with spinal canal 66 (160). The clinician may also align centerline markers 128, 130 with the crest of Ilium bone 62 and reference markers 124A, B with spinal canal 66 when positioning locating guide 120 on patient 18.

The clinician may then obtain a radiographic image of at least a portion of locating guide 120 and underlying tissue of patient 18 near locating guide 120 (162). Upon obtaining the image, the clinician may determine whether one of the foramen apertures 136A-B, 138A-B, 140A-B, 142A-B, and 144A-B is aligned with target nerve site 16 (164). As previously described, foramen apertures 136A-B, 138A-B, 140A-B, 142A-B, and 144A-B provide an opening in locating guide 120 through which the clinician may access target nerve site 16. If one of the foramen apertures 136A-B, 138A-B, 140A-B, 142A-B, and 144A-B is not aligned with target nerve site 16, the clinician may adjust a position of locating guide 120 (160) and generate another medical image. The image and reference markers of locating guide 120 may help indicate the magnitude and direction in which locating guide 120 should be adjusted.

If the medical image indicates that one of the foramen apertures 136A-B, 138A-B, 140A-B, 142A-B, and 144A-B is aligned with target nerve site 16, the clinician may associate at least one of the reference markers of locating guide 120 with target nerve site 16 (166) in order to relate the image to an actual location on patient 18. For example, the clinician may determine which reference markers (e.g., centerline markers 128, 130, lateral markers 132, and/or at least one of foramen aperture 136A, B, 138A, B, 140A, B, 142A, B, and 144A) are closest to target nerve site 16. Based on the associate reference marker(s), the clinician may register the image of target nerve site 16 with an actual location on or within patient 18 (167). Using the associated reference markers to associate the imaged target nerve site 16 with an actual location within patient 18, the clinician may introduce a medical element into patient 18, e.g., with the aid of an introducer needle (168).

Figure 10:
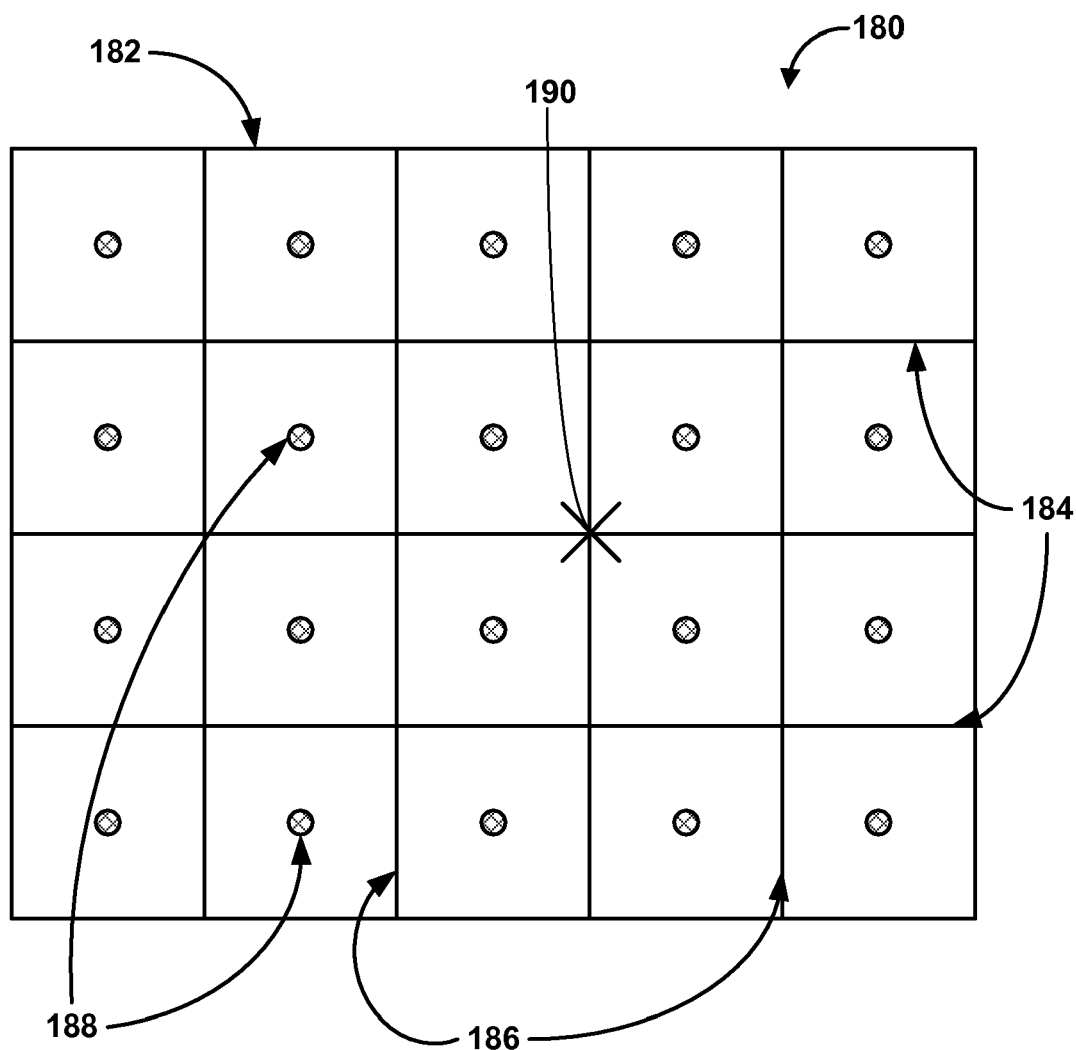
FIG. 10 illustrates a top view of a locating guide in accordance with another embodiment of the invention.

FIG. 10 is a top view of locating guide 180 in accordance with another embodiment. Locating guide 180 includes body 182, a plurality of x-axis reference lines 184, a plurality of y-axis reference lines 186, and lateral markers 188 that extend from body 182 in a general z-axis direction. Orthogonal x-y axes are shown in FIG. 10, and the z-axis extends substantially perpendicular to the plane of the image shown in FIG. 10. In other embodiments, lateral markers 188 may not extend substantially along the z-axis, but extend from body 182 in a direction other than the x-axis and y-axis directions.

Body 182 is formed of a substantially radio-transparent material and reference lines 184, 186 are formed of a substantially radiopaque material, such that body 182 is substantially invisible in a radiographic image and reference lines 184, 186 are substantially visible in the image. Body 182 may be coupled to patient 18 in any of the ways described above with respect to locating guides 30 and 120 of FIGS. 2A-2B and FIGS. 6A-6B, respectively. Body 182 may be any suitable size, which may depend upon the target nerve site 16 that locating guide 180 is used to locate. In embodiments in which target nerve site 16 is a sacral foramen, body 182 may be a quadrilateral having a length and width of about 13 cm to about 15 cm, although other dimensions and shapes are also possible. While the description of locating guide 180 refers primarily to a technique for locating sacral foramen 70, in other embodiments, locating guide 180 may be useful for locating other target nerve sites within patient 18.

In the embodiment shown in FIG. 10, reference lines 184 are spaced about 0.25 cm to about 1.5 cm from an adjacent reference line 184. Similarly, reference lines 186 are spaced about 0.25 cm to about 1.5 cm from an adjacent reference line 186. Reference lines 184, 186 may be separated by other distances in other embodiments. In some embodiments, reference lines 184, 186 may be numbered, e.g., with distance indicators. Lateral markers 188 may be similar to lateral markers 40, 48 of locating guide 30 (FIGS. 2A-B), and are visible in a radiographic image.

Reference lines 184, 186 define a grid that a clinician may refer to when registering a medical image to an actual location on or within patient 18. For example, if a medical image indicates that sacral foramen 70 is located by an intersection 190 between reference lines 184, 186, the clinician may introduce a medical element through body 182 at the relevant intersection 190 on the actual locating guide 180. If, however, the relevant intersection 190 between reference lines 184, 186 is not visible in the medical image, the clinician may associate at least one of lateral markers 188 with the imaged target nerve site. In general, the clinician may use a combination of any of reference lines 184, 186 and lateral markers 188 to relate a medical image to an actual location on patient 18. Reference lines 184, 186 and lateral markers 188 that may directly overlay a target nerve site 16 may provide addition guidance to the clinician when locating target nerve site 16 as compared to locating guide 30 which provides reference markers that surround, rather than overlay, target nerve site 16.

Various embodiments of the invention have been described. Other embodiments of locating guides are also contemplated. For example, while a T-shaped locating guide, a sacral-shaped locating guide, and a substantially quadrilateral locating guide are primarily described above, in other embodiments, a locating guide may include other shapes. In some embodiments, the locating guide may have an L-shape, a substantially circular shape, a substantially elliptical shape, and so forth. In addition, reference markers have any suitable shape, such as substantially rectangular, substantially square, substantially circular, substantially triangular, and so forth. Furthermore, while locating guides (e.g., guide 30 of FIGS. 2A-2B and guide 120 of FIGS. 6A-6B) are described primarily with reference to locating a sacral foramen, in other embodiments, a locating guide may be used to locate other target nerve sites. As one example, a locating guide, such as locating guide 30, may be used to locate a target nerve site within a pelvis, such as the obturator foramen, which may provide access to a pelvic nerve (e.g., the pudendal nerve).

These and other embodiments are within the scope of the following claims.

The invention claimed is:

1. A target tissue site locating guide comprising:
a body defining a major surface;
a first set of substantially radiopaque reference markers on the major surface of the body, wherein at least one reference marker of the first set extends in a first plane; and
a second set of substantially radiopaque reference markers extending laterally from the major surface of the body, wherein at least one reference marker of the second set extends in a second plane, the first plane being different than the second plane, and wherein at least two reference markers of the second set are arranged to be separated from each other along the major surface.

2. The locating guide of claim 1, wherein markers of at least one of the first or second sets of reference markers are integrally formed with the body.

3. The locating guide of claim 1, wherein markers of at least one of the first or second sets of reference markers are fixed to the body.

4. The locating guide of claim 1, wherein the body comprises a substantially radiopaque material.

5. The locating guide of claim 1, wherein the body comprises a substantially radio-transparent material.

6. The locating guide of claim 1, wherein the first set of reference markers extends substantially along the major surface of the body.

7. The locating guide of claim 1, wherein the first set of reference markers comprises at least one reference line printed on the body with a radiopaque material.

8. The locating guide of claim 1, wherein the first set of reference markers comprises a plurality of lines defining a grid.

9. The locating guide of claim 1, wherein the first set of reference markers comprises a plurality of distance markers.

10. The locating guide of claim 1, wherein the first set of reference markers is configured to overlay at least a portion of a boney landmark of a patient.

11. The locating apparatus of claim 10, wherein the boney landmark comprises at least one of an Ilium bone or a spinal canal of the patient.

12. The locating guide of claim 1, wherein the second set of reference markers is oriented at an angle relative to the major surface of the body.

13. The locating guide of claim 12, wherein the angle is in a range of about 45 degrees to about 100 degrees.

14. The locating guide of claim 13, wherein the angle is about 60 degrees.

15. The locating guide of claim 13, wherein the angle is about 90 degrees.

16. The locating guide of claim 1, wherein markers of the second set of reference markers extends from the major surface of the body about 0.25 cm to about 2 cm.

17. The locating guide of claim 1, further comprising a centerline marker positioned along a center axis of the body.

18. The locating guide of claim 1, wherein the body defines a first portion and a second portion substantially perpendicular to the first portion.

19. The locating guide of claim 18, wherein at least one of the first portion or the second portion of the body is configured to substantially conform to a size and shape of at least a portion of a boney landmark of a patient.

20. The locating guide of claim 19, wherein the first portion of the body is configured to substantially overlay at least a portion of an Ilium bone of a patient and the second portion of the body is configured to substantially overlay at least a portion of a spinal canal of the patient.

21. The locating guide of claim 1, wherein the body defines a first shape substantially corresponding to a second shape defined by a human sacrum.

22. The locating guide of claim 21, wherein the body defines at least one aperture configured to receive an introducer for a medical element.

23. The locating guide of claim 1, further comprising a third reference marker extending substantially perpendicular to the first set of reference markers along the major surface of the body.

24. The locating guide of claim 1, wherein the body defines at least one aperture configured to receive an introducer for a medical element.

25. The locating guide of claim 1, further comprising an adhesive along a skin contact surface of the body.

26. A method comprising:
    positioning a locating guide on a skin surface of a patient, wherein the locating guide comprises:
        a body defining a major surface;
        a first set of radiopaque reference markers on the major surface of the body,
    wherein at least one reference marker of the first set extends in a first plane; and
        a second set of radiopaque reference markers configured to extend laterally from the major surface of the body, wherein at least one reference marker of the second set extends in a second plane, the first plane being different than the second plane, wherein markers of one of the first set or the second set of radiopaque references markers are configured to extend away from the skin surface of the patient when the locating guide is positioned on the skin surface, and wherein at least two reference markers of the second set are arranged to be separated from each other along the major surface;
    generating an image of at least a portion of the locating guide and at least a portion of tissue of the patient proximate to the locating guide with a medical imaging device; and
    registering the image with an actual location on or within the patient based on at least one of the first or second reference markers.

27. The method of claim 26, wherein the image comprises a radiographic image.

28. The method of claim 26, wherein registering the image comprises:
    identifying at least one marker of the first set of reference markers of the locating guide in the first image; and
    identifying at least one marker of the second set of reference markers of the locating guide in the second image.

29. The method of claim 26, further comprising identifying a first location of a target tissue site within the tissue based on the image, wherein registering the image comprises registering the first location of the target tissue site with a second location on the skin surface of the patient based on markers of at least one of the first or second sets of reference markers.

30. The method of claim 29, wherein the first set of reference markers of the locating guide comprises a plurality of lines defining a grid, and registering the first location of the target tissue site with the second location on the skin surface of the patient based on markers of at least one of the first or second sets of reference markers comprises identifying, within the image, an intersection of the grid proximate to the target tissue site.

31. The method of claim 29, wherein the first set of reference markers of the locating guide comprises a plurality of substantially radiopaque distance markers that indicate a distance along the body, and registering the first location of the target tissue site with the second location on the skin surface of the patient based on at least one of the first or second sets of reference markers comprises:
    identifying, within the image, at least one of the plurality of distance markers proximate to the target tissue site; and identifying the at least one of the plurality of distance markers proximate to the target tissue site on the locating guide.

32. The method of claim 29, further comprising introducing a medical device into the patient proximate to the target tissue site within the patient.

33. The method of claim 32, wherein the body of the locating guide defines an aperture, and wherein introducing the medical device into the patient comprises introducing the medical device into the patient through the aperture.

34. The method of claim 32, wherein introducing the medical device into the patient comprises introducing an introducer needle into the patient, the method further comprising orienting the introducer needle to substantially match an orientation of the second reference marker relative to the skin surface.

35. The method of claim 26, wherein positioning the locating guide on the skin surface of the patient comprises:
   locating a boney landmark of the patient; and
   positioning the first reference marker of the locating guide on the skin surface of the patient proximate to the boney landmark.

36. The method of claim 26, wherein the image comprises a first image of a first perspective of the locating guide, the method further comprising generating a second image of a second perspective of at least a portion of the locating guide and at least a portion of tissue of the patient proximate to the locating guide with the medical imaging device.

* * * * *